(12) United States Patent
Kessler et al.

(10) Patent No.: US 9,441,025 B2
(45) Date of Patent: Sep. 13, 2016

(54) PRAME DERIVED PEPTIDES AND IMMUNOGENIC COMPOSITIONS COMPRISING THESE

(71) Applicant: Academisch Ziekenhuis Leiden h.o.d.n. LUMC, Leiden (NL)

(72) Inventors: Jan Kessler, Leiden (NL); Marieke Griffioen, Alphen a/d Rijn (NL); Cornelis Johannes Maria Melief, Haarlem (NL); Jan Wouter Drijfhout, Leiden (NL)

(73) Assignee: Academisch Ziekenhuis Leiden H.O.D.N. LUMC, Leiden (NL)

( * ) Notice: Subject to any disclaimer, the term of this patent is extended or adjusted under 35 U.S.C. 154(b) by 118 days.

(21) Appl. No.: 13/945,335

(22) Filed: Jul. 18, 2013

(65) Prior Publication Data

US 2014/0348862 A1 Nov. 27, 2014

Related U.S. Application Data

(60) Division of application No. 12/586,625, filed on Sep. 24, 2009, now Pat. No. 8,492,514, which is a continuation of application No. PCT/NL2008/050171, filed on Mar. 26, 2008.

(30) Foreign Application Priority Data

Mar. 26, 2007 (EP) .................................. 07104893

(51) Int. Cl.
*A61K 38/00* (2006.01)
*C07K 14/47* (2006.01)
*A61K 39/00* (2006.01)

(52) U.S. Cl.
CPC ....... *C07K 14/4748* (2013.01); *A61K 39/0011* (2013.01); *A61K 39/00* (2013.01); *A61K 2039/57* (2013.01); *A61K 2039/572* (2013.01)

(58) Field of Classification Search
None
See application file for complete search history.

(56) References Cited

U.S. PATENT DOCUMENTS

| | | | |
|---|---|---|---|
| 5,830,753 A | 11/1998 | Coulie et al. | ............. 435/325 |
| 6,022,692 A | 2/2000 | Coulie et al. | ............. 435/6 |
| 6,297,050 B1 | 10/2001 | Coulie et al. | ............. 435/372.3 |
| 6,339,149 B1 | 1/2002 | Coulie et al. | ............. 536/23.5 |
| 7,820,786 B2 | 10/2010 | Thomson et al. | |
| 2005/0022144 A1 | 1/2005 | Wang | ............. 716/5 |
| 2005/0221440 A1 | 10/2005 | Simard et al. | |
| 2011/0269949 A1 | 11/2011 | Qiu et al. | ............. 536/23.5 |

FOREIGN PATENT DOCUMENTS

| | | | |
|---|---|---|---|
| EP | 0783511 | 7/1997 | ............. A61K 35/14 |
| WO | WO 96/10577 | 4/1996 | ............. C07H 21/04 |
| WO | WO-01/52612 | 7/2001 | |
| WO | WO 01/52614 A2 | 7/2001 | |
| WO | WO 01/90197 | 11/2001 | ............. C07K 19/00 |
| WO | WO 03/084467 | * 4/2003 | |
| WO | WO 2006/009920 A2 | 1/2006 | ............. C07K 14/47 |

OTHER PUBLICATIONS

Zwaveling et al, J Immunol, 2002; 169:350-358.*
Lee et al, J. Immunol., 1999, 163:6292-6300.*
Marincola et al, Trends in Immunology, Jun. 2003, 334-341.*
Kirkin, et al., 1998, APMIS, 106 : 665-679.*
Chaux et al, Int J Cancer, 1998, 77: 538-542.*
Celis, J of Clinical Investigation, 2002, 110:1765-1768.*
Harlin et al, Caner Immunol. Immunotherap. 2006, 55:1185-1197.*
Chamberlain et al Expert Opinion on Pharmacotherapy, 1(4): 603-614, 2000.*
Byers, "What Can Randomized Controlled Trials Tell US About Nutrition and Cancer Prevention?," CA Cancer J Clin, vol. 49, No. 6, Dec. 1999, pp. 353-361.
Granziero, et al. "Adoptive immunotherapy prevents prostate cancer in a transgenic animal model", European Journal of Immunology (1999) vol. 29, pp. 1127-1138.
Gura, "Systems for Identifying New Drugs Are Often Faulty", Science (Nov. 7, 1997), vol. 278, pp. 1041-1042.
Johnson, et al. "Peptide and Protein Drug Delivery", Encyclopedia of Controlled Drug Delivery (1999), vol. 2, pp. 816-833.
Kaiser, "First Pass at Cancer Genome Reveals Complex Landscape", Science, (Sep. 8, 2006), vol. 313, p. 1370.
Ikeda H., et al., "Characterization of an Antigen That Is Recognized on a Melanoma Showing Partial HLA Lossby CTL Expressing an NK Inhibitory Receptor", Immunity, vol. 6, 199-208, Feb. 1997.
Epping, et al., "The Human Tumor Antigen PRAME is a Dominant Repressor of Retinoic Acid Receptor Signaling", Cell, vol. 122, pp. 835-847, Sep. 23, 2005.
Kawahara, M. et al., "Identification of HLA class I-restricted tumor-associated antigens in adult T cell Leukemia cells by mass spectrometric analysis", Experimental Hematology 34, pp. 1496-1504, 2006.

* cited by examiner

*Primary Examiner* — Mark Halvorson
(74) *Attorney, Agent, or Firm* — Foley & Lardner LLP; Sunit Talapatra

(57) ABSTRACT

The invention relates to a peptide having a length of no more than 100 amino acids and comprising at least 19 contiguous amino acids from the amino acid sequence of the human PRAME protein, wherein the peptide comprises at least one HLA class II epitope and at least one HLA class I epitope from the amino acid sequence of the human PRAME protein and to its use as such or in a composition as a medicament for the treatment and/or prevention of cancer.

10 Claims, 6 Drawing Sheets

Figure 1

| Start | End | Sequence |
|---|---|---|
| 1 | 27 | M E R R R L W G S I Q S R Y I S M S V W T S P R R L V |
| 19 | 45 | V W T S P R R L V E L A G Q S L L K D E A L A I A A L |
| 37 | 63 | D E A L A I A A L E L L P R E L F P P L F M A A F D G |
| 53 | 79 | F P P L F M A A F D G R H S Q T L K A M V Q A W P F T |
| 70 | 96 | K A M V Q A W P F T C L P L G V L M K G Q H L H L E T |
| 84 | 110 | G V L M K G Q H L H L E T F K A V L D G L D V L L A Q |
| 90 | 116 | Q H L H L E T F K A V L D G L D V L L A Q E V R P R R |
| 98 | 124 | K A V L D G L D V L L A Q E V R P R R W K L Q V L D L |
| 116 | 142 | R W K L Q V L D L R K N S H Q D F W T V W S G N R A S |
| 133 | 159 | W T V W S G N R A S L Y S F P E P E A A Q P M T K K R |
| 153 | 179 | Q P M T K K R K V D G L S T E A E Q P F I P V E V L V |
| 173 | 199 | I P V E V L V D L F L K E G A C D E L F S Y L I E K V |
| 182 | 208 | F L K E G A C D E L F S Y L I E K V K R K K N V L R L |
| 203 | 229 | K N V L R L C C K K L K I F A M P M Q D I K M I L K M |
| 239 | 265 | E V T C T W K L P T L A K F S P Y L G Q M I N L R R L |
| 247 | 273 | P T L A K F S P Y L G Q M I N L R R L L S H I H A S |

Figure 1 (Continued)

| | | |
|---|---|---|
| 269 | 295 | H I H A S S Y I S P E K E E Q Y I A Q F T S Q F L S L |
| 290 | 316 | S Q F L S L Q C L Q A L Y V D S L F F L R G R L D Q L |
| 311 | 337 | G R L D Q L L R H V M N P L E T L S I T N C R L S E G |
| 323 | 349 | P L E T L S I T N C R L S E G D V M H L S Q S P S V S |
| 343 | 365 | S Q S P S V S Q L S V L S L S G V M L T D V S |
| 359 | 385 | V M L T D V S P E P L Q A L L E R A S A T L Q D L V F |
| 372 | 398 | L L E R A S A T L Q D L V F D E C G I T D D Q L L A L |
| 384 | 410 | V F D E C G I T D D Q L L A L L P S L S H C S Q L T T |
| 399 | 423 | L P S L S H C S Q L T T L S F Y G N S I S I S A L |
| 415 | 441 | G N S I S I S A L Q S L L Q H L I G L S N L T H V L Y |
| 424 | 450 | Q S L L Q H L I G L S N L T H V L Y P V P L E S Y E D |
| 444 | 470 | P L E S Y E D I H G T L H L E R L A Y L H A R L R E L |
| 460 | 486 | L A Y L H A R L R E L L C E L G R P S M V W L S A N P |
| 473 | 499 | E L G R P S M V W L S A N P C P H C G D R T F Y D P E |
| 483 | 509 | S A N P C P H C G D R T F Y D P E P I L C P C F M P N |

Figure 4

HLA class I binding peptides[a]

HLA-A3 binding: C L P L G V L M K
HLA-A24 binding: P F T C L P L G V L

Digestion PRAME 70-96

| Position | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | Fragment[b] Start | End | Intensity (%)[c] 1 h |
|---|---|---|---|---|---|---|---|---|---|---|---|---|---|---|---|---|---|---|---|---|---|---|---|---|---|---|---|---|---|---|
| Substrate | K | A | M | V | Q | A | W | P | F | T | C | L | P | L | G | V | L | M | K | G | Q | H | L | H | L | E | T | | | |
| Fragments | | | | V | Q | A | W | | | | | | | | | | | | | | | | | | | | | 73 | 76 | 3.0 |
| | | | | | Q | A | W | | | | | | | | | | | | | | | | | | | | | 74 | 76 | 8.3 |
| | | | | | | A | W | P | F | | | | | | | | | | | | | | | | | | 75 | 78 | 1.6 |
| | | | | | | | | P | F | T | C | L | P | L | G | V | L | | | | | | | | | | 77 | 86 | 4 |
| | | | | | | | | | | T | C | L | P | L | G | V | L | | | | | | | | | | 79 | 86 | 46 |
| | | | | | | | | | | | | | P | L | G | V | L | M | | | | | | | | | 82 | 87 | 7.7 |
| | | | | | | | | | | | | | | | G | V | L | M | K | | | | | | | | 84 | 88 | 2.6 |
| | | | | | | | | | | | | | | | | V | L | M | K | G | | | | | | | 85 | 89 | 2.6 |
| | | | | | | | | P | F | T | C | L | P | L | G | V | L | M | K | G | Q | H | L | H | L | E | T | 77 | 96 | 19.6 |
| | | | | | | | | | | | | | P | L | G | V | L | M | K | G | Q | H | L | H | L | E | T | 82 | 96 | 4.4 |

Not intact in digestion fragments
Intact in digestion fragments

US 9,441,025 B2

PRAME DERIVED PEPTIDES AND IMMUNOGENIC COMPOSITIONS COMPRISING THESE

RELATED APPLICATIONS

This present invention is a divisional application of U.S. Ser. No. 12/586,625, filed Sep. 24, 2009, which is a continuation patent application that claims priority to PCT patent application number PCT/NL2008/050171, filed Mar. 26, 2008 and claims priority to European Patent Application No. 07104893.8, filed Mar. 26, 2007, the entirety of which are herein incorporated by reference.

SEQUENCE LISTING

The instant application contains a Sequence Listing which has been submitted electronically in ASCII format and is hereby incorporated by reference in its entirety. Said ASCII copy, created on Aug. 13, 2015, is named 069818-0411_SL.txt and is 32,584 bytes in size.

FIELD OF THE INVENTION

The present invention relates to the field of medicine and immunology. In particular it relates to peptides, vaccines and methods for preparing vaccine compositions that are capable of eliciting anti-tumor cell immune responses in vivo when administered to a subject.

BACKGROUND OF THE INVENTION

The tumor-associated antigen PRAME (PReferentially expressed Antigen in MElanoma cells) was originally identified as an antigen recognized by cytotoxic T lymphocytes capable of lysing melanoma cells (Ikeda et al., Immunity. 1997; 6:199-208.) Although the tumor antigen PRAME is known to be overexpressed in a wide variety of human cancers, its molecular function has remained unclear until recently. PRAME was recently identified as a dominant repressor of RAR (retinoic acid receptor) signalling. PRAME was shown to bind RAR in the presence of RA, preventing ligand-induced receptor activation and target gene transcription through recruitment of Polycomb proteins. PRAME was shown to be present at RAR target promoters and inhibited RA-induced differentiation, growth arrest, and apoptosis. Conversely, inhibition of PRAME expression by RNA interference in RA-resistant human melanoma restored RAR signalling and reinstated sensitivity to the antiproliferative effects of RA in vitro and in vivo. (Epping et al., Cell. 2005; 122(6): 835-47). Overexpression of PRAME, as is frequently observed in human malignancies, may provide tumor cells growth and survival advantages by antagonizing RAR signalling.

PRAME has in fact been found to be overexpressed in a broad array of solid tumors and 30% of acute leukaemia's, whereas normal tissue expression is confined to the testis, endometrium and at very low levels in ovaries and adrenals. It is an established tumor antigen and its potential application as target for immunotherapies is well documented in art, as discussed in U.S. Pat. No. 5,830,753, U.S. Pat. No. 6,297,050, U.S. Pat. No. 6,339,149, EP 0783511 B1, WO 01/52612 and US 2005/0221440 A1. Despite many publications that indicate the potential of PRAME as a tumor antigen and attractive candidate target of eliciting anti-tumor cell immune responses and preparing anti-tumor vaccines, little data are available that substantiate the natural preservation of the PRAME derived peptides and epitopes, neither were data available showing the immunogenicity of these epitopes, which is needed to establish an effective anti-tumor T-cell response. The current invention addresses this problem and provides improved PRAME derived peptides comprising newly identified MHC class I and II epitopes and compositions comprising these peptides.

SUMMARY OF THE INVENTION

U.S. Pat. No. 6,297,050, WO01/52612 and US 2005/0221440A1 provide PRAME derived nucleic acid molecules, encoding epitopes and peptides that comprise these epitopes. PRAME derived and/or PRAME epitope containing peptides disclosed in the prior art may be applied as active constituents of compositions for vaccination. Such peptides were based on HLA class I presented epitopes that were identified by binding prediction algorithms and determination of proteasomal cleavages, but did not take account of the fact that for optimal induction of CD8$^+$ CTL responses the selected sequences need to include both sequences presented by HLA class I molecules and HLA class II molecules. Moreover, no data are provided as to whether these epitopes and peptides are actually capable of mounting an immune response in humans in vivo.

The current invention provides peptides and compositions capable of eliciting both CD4$^+$ T helper lymphocytes (Th cells) and CD8$^+$ cytotoxic T lymphocytes (CTL) responses. A major objective of the present invention is providing new anti-tumor PRAME epitope containing peptides and compositions for vaccination purposes comprising these, which are more effective due to the presence of both confirmed CD4$^+$ Th and CD8$^+$ CTL epitopes. The peptide containing compositions of the invention can be synthetically made and are therefore completely defined, which is advantageous for manufacturing, quality control and safety assurance purposes. The peptides of the invention are optimally designed to be used as a vaccine to induce a strong therapeutic and/or protective immune response, against PRAME expressing malignancies by inducing simultaneously CD4$^+$ Th and CD8$^+$ CTL responses and are applicable for a high percentage of the patients because the HLA class I and HLA class II epitopes contained in these peptides have a broad HLA haplotype coverage.

The current invention provides improved peptides derived from the PRAME protein comprising newly identified epitopes. PRAME derived peptide sequences according to this invention meet a number of strict requirements: they are small enough to be efficiently synthesized yet large enough to be taken up by professional antigen presenting cells. Peptides according to the invention can be readily degraded by the 20S proteasome, releasing HLA class I presentable fragments or epitopes. The peptides according to the invention preferably comprise at least one HLA class I and at least one HLA class II epitope. The HLA class II-presentable epitopes are excised from the peptides of the invention by a proteasome-independent route. It is essential that these class II epitopes are present for optimal CD8$^+$ effector T cell and CD8$^+$ memory T cell formation, because CD4$^+$ Th cells provide the necessary signals to dendritic cells (DC) to allow these DC to induce optimal robust CD8$^+$ effector as well as memory T cell responses. The epitopes present in peptides of the invention can be displayed on a wide range of HLA class I and HLA class II molecules of a wide range of MHC haplotypes, in particular the most predominant of these HLA molecules in humans, which covers most HLA haplotypes in patients. The peptides of the invention comprise HLA-A1, HLA-A2, HLA-A3, HLA-A24, HLA-A68, HLA-B7, HLA-B8, HLA-B35, HLA-B60, HLA-B61 and HLA-B62 presented cytotoxic T lymphocyte (CTL) epitopes, of which both the HLA class I binding capacity and the C-terminal generation by the proteasome has been established experimentally. The HLA-A2 binding CTL epitope containing peptides are the most preferred, as HLA-A2 is the most predominant HLA class I molecule in humans.

Peptides according to this invention in addition preferably have a proven CD4+ Th cell reactivity, as determined by ex vivo analysis in healthy controls and/or in cancer patients, thereby ensuring not only improved CD8+ effector T-cell generation but also proper CTL memory. In addition, the HLA class I binding CTL epitopes present in the peptides of the invention preferably have a proven CD8+ CTL cell stimulating activity, confirmed either by their capacity to induce CTL in vitro and/or in vivo in healthy donors and/or in cancer patients.

In particular the invention discloses a group of 20 PRAME derived peptides of 33 to 35 consecutive amino acids (aa.) from the PRAME amino acid sequence, fulfilling most or all the requirements set out above and which may be used separately, or in any combination of 2, 3, 4, 5, 10, up to all 20 peptides, for use in the treatment or prevention of malignancies or cancer, and to be provided in compositions for vaccination for the treatment and/or prevention of PRAME (over-)expressing malignancies, in particular tumors. The invention hence discloses immunogenic compositions comprising at least 1 and preferably 2 or more peptides of the group of 20 PRAME derived peptides. The immunogenic compositions preferably further comprise immune modulators and adjuvants, more preferably synthetic adjuvants, that have been selected to greatly enhance and optimize the immunogenic activity of the peptides and epitopes of the invention that display anti-tumor activity in vitro and/or in vivo.

DESCRIPTION OF THE INVENTION

Anti-tumor vaccines find their application in many therapeutic fields ranging from anti-cancer treatments to treatment or prophylaxis of malignancies such as virally induced malignancies, comprising Human papilloma virus (HPV), Kaposi sarcoma herpes virus (KSHV), Epstein Bar virus induced lymphoma's (EBV), but also sporadic malignancies that display tumor antigens such as MAGE, BAGE, RAGE, GAGE, SSX-2, NY-ESO-1, CT-antigen, CEA, PSA, p53 or PRAME. The most preferred immune response to be obtained by any anti-tumor peptide vaccine is a T cell response, elicited by T cell epitopes within the peptides. A successful anti-tumor T-cell response should consist of both an HLA class I restricted CTL response and simultaneously an HLA class II restricted Th response, and may be advantageously accompanied by a B-cell response. Several publications have demonstrated that CD4+ T-cells upon interaction with class II epitope presenting dendritic cells (DC) upregulate CD40 ligand.

The interaction of the CD4+ Th cell by its CD40 ligand with the CD40 molecule on the DC leads to activation of the DC. Activated DCs display upregulated costimulatory molecules and secrete CTL-promoting cytokines. This not only allows a more robust CD8+ CTL response induced by such an activated DC that presents MHC class I restricted epitopes, but also a much more robust CTL memory response (Ridge et al. 1998, Nature 393:474; Schoenberger et al. 1998, Nature 393:480; Sun et al. 2004, Nat. Immunol. 5:927). The need for CD40 expression on DC for robust anti-tumor CD8+ CTL responses following vaccination with long (35 aa.) peptides was published in Zwaveling et al. (2002, J. Immunol. 169:350). Recently we have found that without the induction of CD4+ Th responses by MHC class II epitopes contained in the long peptides, the induced CD8+ CTL responses are less vigorous and short lived, completely lacking CD8+ CTL memory.

HLA class I presented cytotoxic T lymphocyte (CTL) epitopes encoded by PRAME are produced intracellularly, by a sequence of defined intracellular mechanisms, from either full length PRAME protein molecules or from shorter PRAME encoded defective ribosomal products (DRIPS; Yewdell et al., 2002, Mol. Immunol 39:139).

First, the dominant event that defines a CTL epitope is the release of the epitope (or epitope-precursor) from its flanking protein regions through enzymatic digestion by cytosolic peptidases. The multicatalytic proteasome is the primary enzyme complex considered to be required for the generation of the exact C-terminus of the vast majority of CTL epitopes (Rock et al., 2004, Nat. Immunol. 5:670). The generation of the amino-terminus of a CTL epitope, at the other hand, is much more flexible because several amino-terminal exo-peptidases (like ERAP1, puromycin sensitive aminopeptidase, bleomycin hydrolase and others) reside in the cytosol and endoplasmic reticulum (ER) and those trimming enzymes have the capacity to shorten an N-terminal elongated epitope-precursor to its precise length. In contrast, C-terminal trimming has not been reported. Therefore, experimental determination of proteasomal cleavage sites in the PRAME protein identifies the C-termini of endogenously produced PRAME peptide fragments that may bind HLA class I molecules. In special cases, mostly involving CTL epitopes with a basic C-terminal residue, a non-proteasomal enzyme activity is needed for the generation of the epitope's C-terminus (see Tenzer et al., 2005; Cell. Mol. Life Sci 62:1025 and Seifert et al., 2003, Nat. Immunol. 4:375). The current invention also discloses a novel HLA-A3 presented CTL epitope that we identified to be C-terminally produced by a non-proteasomal dual action of the enzymes Nardilysin (EC 3.4.24.61) and Thimet oligopeptidase (TOP) (EC 3.4.24.15).

Secondly, enzymatically generated peptide fragments—with a length of 9-11 aa.—should have binding capacity for the HLA class I molecules available in the cells where they are produced. Binding of peptides to HLA class I molecules is restricted to those peptides that possess the required aa. residues at the so-called anchor positions. Due to the highly polymorphic HLA molecules, each class I molecule has a distinct preferred binding motif, comprising preferred anchor residues.

Both phenomena, enzymatic digestion, mostly by the proteasome, and HLA class I peptide binding, may be tested experimentally, and the combination of the results of such tests allows the reliable and precise selection of HLA class I presented CTL epitopes (Kessler et al., 2001, J. Exp. Med. 173:73). Additionally, to confirm the usefulness of the identified putative HLA class I presented CTL epitopes from PRAME, the synthetic epitope peptides may be tested for their immunogenic capacity to induce in vitro CTL responses. Once a CTL line that is reactive against the identified epitope has been generated, this CTL line (or clones derived from that line) may be used to confirm the cell surface expression of the CTL epitope on the tumor cell by functional CTL recognition assays (Kessler et al., 2001, J. Exp. Med. 173:73).

The present invention provides carefully selected peptide sequences derived from the intact human PRAME protein antigen. Such peptides result in a much improved, enhanced and prolonged CD8⁺ CTL effector and memory response upon administration in a wide range of patients with PRAME-positive cancer. Newly identified CD4+ Th and CD8⁺ CTL cell epitopes in PRAME, as well as PRAME derived synthetic peptides and immunogenic compositions comprising these are also part of the present invention.

Since the peptides of the invention are preferably used as a vaccine alone or in combination or as part of an immunogenic composition, the peptides are preferably named vaccine peptides and the composition vaccine compositions.

The use of relatively short peptides is highly preferred for medical purposes as these can be synthesized in vitro efficiently, which is not possible or uneconomical for native proteins larger than about 100 amino acids. Chemical synthesis of peptides is routine practice and various suitable methods are known to the skilled person. Chemical synthesis of peptides also overcomes the problems associated with recombinant production of intact proteins, which is difficult to standardize and requires extensive purification and quality control measures. Peptides with a length that exceeds the length of HLA class I and class II epitopes (e.g. having a length as indicated below herein) are particularly advantageous for use as vaccine component because they are large enough to be taken up by professional antigen presenting cells, in particular DC, as explained in WO02/070006 and processed in the DC before cell surface presentation of the contained HLA class I and class II epitopes takes place. Therefore, the disadvantageous induction of T cell tolerance by the systemic presentation of minimal HLA class I epitopes on non-antigen presenting cells (as shown in Toes et al., 1996, Proc. Natl. Acad. Sci. U.S.A 93:7855 and Toes et al., 1996, J. Immunol. 156:3911), is prevented by the application of peptides of the invention having a length as indicated herein (as shown in Zwaveling et al., 2002, J. Immunol. 169:350).

Peptides comprising epitopes which are to be presented to T cell receptors of CTL and/or Th cells preferably fulfil a number of requirements. The peptides preferably have sufficient length to contain both HLA class I and HLA class II epitopes. Furthermore, the peptides preferably comprise anchor residues within their HLA class I and II binding parts to enable binding to the class I and II molecules, respectively. The stability of the interaction between peptide and presenting MHC molecule should be sufficient in order to generate a significant and effective immune response. In the context of the present invention, the stability of the interaction between peptide and presenting MHC molecule is considered to be sufficient in this respect if the peptide has an intermediate to high affinity binding, whereby an $IC_{50} \geq$ about 5 μM is considered high affinity binding, about 5 μM<$IC_{50} \geq$ about 15 μM is considered intermediate affinity binding, about 15 μM<$IC_{50} \leq$ 100 μM is judged low affinity binding and $IC_{50}$>about 100 μM was regarded as no binding.

A specific proteasomal cleavage site generating the C-terminus of the epitope, preferably is present exactly after the epitope aa. sequence in order to be liberated from the larger peptide and presented on the HLA class I molecule. Length requirements are much less strict for HLA class II presented epitopes, therefore a need for precise enzymatic generation of the class II binding peptide is less absolute. These requirements have been used in the present invention to localize and design peptides in the full length PRAME protein sequence that comprise combinations of preferred CTL and Th cell epitopes and are thus highly suitable peptides for vaccination purposes.

Moreover, in vitro and ex vivo T cell experiments are preferably used to confirm the capability of peptides according to the invention to induce substantial CD4⁺ Th and CD8⁺ CTL responses. The peptides of the present invention thereby provide a marked improvement in the selection of relatively short peptides that may be chemically synthesized, comprising the most potent and most widely applicable HLA class I and class II presented T cell epitopes derived from the PRAME tumor antigen. The peptides are particularly optimized with respect to their proteasomal cleavage and preferably contain both HLA class I and class II epitopes. The liberation of the C-termini of CTL epitopes contained within the peptides of the invention by the 20S proteasome provide HLA class I binding fragments with CD8⁺ CTL stimulatory capacity.

In a first aspect of the invention there is provided a peptide comprising a contiguous amino acid sequence selected from the 509 amino acid sequence of the human PRAME protein, depicted in SEQ ID No. 21, whereby the peptide preferably comprises at least one HLA class II Th cell epitope and preferably also at least one HLA class I cytotoxic T cell epitope. Preferably the peptide has a length of no more than 100 amino acids and comprises at least 19 contiguous amino acids selected from the amino acid sequence of the human PRAME protein (i.e. SEQ ID No. 21), wherein the peptide preferably comprises at least one HLA class II epitope and preferably also at least one HLA class I epitope, preferably (but not necessarily) both from the amino acid sequence of the human PRAME protein. More preferably, in the peptide at least one HLA class II epitope and at least one HLA class I epitope are present within a contiguous amino sequence from the amino acid sequence of the human PRAME protein.

For the sake of clarity, the peptide of the invention preferably comprises at least one HLA class I presented epitope and preferably also at least one HLA class II presented epitope. Each of these epitopes are presentable and will bind to the corresponding specific HLA molecule present on the cells after having been processed as described herein. Each HLA epitope may therefore also be named a HLA binding and/or presentable epitope.

The length of the contiguous amino acid sequence from the human PRAME protein comprised within the peptide, preferably is at least 19, 20, 21, 22, 25, 27, 30, 33 or 35 amino acids and preferably no more than 100, 80, 60, 50, 45, 40, 35, 33 or 30 amino acids, more preferably the length of the contiguous amino acid sequence from the human PRAME protein comprised within the peptide is 19-45, even more preferably 30-40 amino acids, even more preferably 30-35 and most preferably 33-35 amino acids. In another preferred embodiment, the peptide of the invention consists of any of the contiguous amino acid sequence from the human PRAME protein as defined herein. The peptides of the invention may be easily synthesized and are large enough to be taken up by professional antigen presenting cells, processed by the proteasome and have sufficient physical capacity and length to contain at least one HLA class I and one HLA class II epitope. Optionally a peptide may comprise N- or C-terminal extensions, which may be amino acids, modified amino acids or other functional groups that may for instance enhance bio-availability, cellular uptake, processing and/or solubility.

Preferably, the class II CD4⁺ Th cell epitope comprised in a peptide according to the invention is capable of activating a CD4⁺ Th cell in human cancer patient and/or a healthy control. The activation is preferably assessed ex vivo or in vivo, more preferably in the human cancer patient whose tumor cells express the PRAME antigen. Most preferably, the HLA class II epitope is capable of activating a CD4+ Th memory response, i.e. activation of a CD45RO-positive CD4+ Th cell. This will lead, by virtue of the 'license to kill' signal through CD40-triggering of DC (Lanzavecchia, 1998, Nature 393:413), to a more robust CD8+ effector and memory CTL response.

A peptide of the invention further comprises an HLA class I epitope. Said HLA class I epitope is preferably C-terminally processed by proteasomal cleavage. In addition, said HLA class I epitope is preferably capable of activating a CD8+ CTL response. Most preferably, the CTL activating capability has been demonstrated ex vivo and/or in vivo, in human healthy control individuals or even more preferably in human cancer patients. Preferably, in the human cancer patients the tumor expresses the PRAME antigen. The presence of both an HLA class I and class II epitope within one peptide has been observed to be particularly advantageous due to synergy in mounting and maintaining an effective CTL cell response (as shown in Zwaveling et al., 2002, J. Immunol. 169:350).

The HLA class I epitopes in the PRAME peptides of the invention are preferably capable of being presented on HLA alleles that are predominant in the population of human subjects to be treated. Preferred HLA class I epitopes in PRAME derived peptides of the invention are epitopes capable of binding to HLA-A1, HLA-A2, HLA-A3, HLA-A24, HLA-A68, HLA-B7, HLA-B8, HLA-A35, HLA-B60, HLA-B61 and HLA-B62. The most preferred HLA class I CTL epitopes are the HLA-A2 binding PRAME epitopes, because HLA-A2 is highly predominant in all of the Caucasian, black, Indian-American and oriental populations, as indicated in table 1. The HLA class I epitope preferably has a high peptide binding capacity ($IC_{50}$<about 5 µM peptide) or at least intermediate affinity (5 µM<$IC_{50}$<about 15 µM peptide).

According to a more preferred embodiment, peptides of the invention have a length of no more than 100 amino acids and comprise a contiguous amino acid sequence from the human PRAME protein selected from the group consisting of amino acid sequences SEQ ID No's 1-20 or selected from the group consisting of amino acid sequences SEQ ID NO 6, 5, 7, 8, 9, 10, 11, 12, 14, 15, 16, 18, 1, 2, 3, 4, 13, 17, 19 and SEQ ID NO:20: aa. 1-33 of the human PRAME protein is represented by SEQ ID NO. 1, aa. 19-53 (SEQ ID NO. 2), aa. 47-79 (SEQ ID NO. 3), aa. 69-101 (SEQ ID NO. 4), aa. 80-114 (SEQ ID NO. 5), aa. 94-126 (SEQ ID NO. 6), aa. 112-144 (SEQ ID NO. 7), aa. 133-166 (SEQ ID NO. 8), aa. 173-207 (SEQ ID NO. 9), aa. 190-223 (SEQ ID NO. 10), aa. 234-268 (SEQ ID NO. 11), aa. 247-279 (SEQ ID NO. 12), aa. 262-294 (SEQ ID NO. 13), aa. 284-316 (SEQ ID NO. 14), aa. 295-327 (SEQ ID NO. 15), aa. 353-387 (SEQ ID NO. 16), aa. 399-431 (SEQ ID NO. 17), aa. 417-450 (SEQ ID NO. 18), aa. 447-480 (SEQ ID NO. 19), aa. 477-509 (SEQ ID NO. 20). The full length amino acid sequence of the human PRAME protein is given in SEQ ID No. 21.

Even more preferred peptides within this group include SEQ ID No's 6, 5, 7, 8, 9, 10, 11, 12, 14, 15, 16, and 18, which comprise HLA-A2 or other predominant HLA class I epitopes. The most preferred peptides of the invention within this subgroup include SEQ ID No's 6, 5, 8, 14, 15, 16 and 18, all of which comprise an HLA-A2 binding epitope that has been demonstrated to induce CTL that recognize the naturally presented epitope when endogenously processed from the PRAME tumor antigen.

The PRAME derived peptides of the invention may be modified by deletion or substitution of one or more amino acids, by extension at the N- and/or C-terminus with additional amino acids or functional groups, which may improve bio-availability, targeting to T-cells, or comprise or release immune modulating substances that provide adjuvant or (co)stimulatory functions. The optional additional amino acids at the N- and/or C-terminus are preferably not present in the corresponding positions in the PRAME amino acid sequence, more preferably they are not from the PRAME amino acid sequence (SEQ ID NO. 21). The skilled person will appreciate that PRAME amino acid sequences of naturally occurring human allelic variants of PRAME are expressly included in the invention.

The PRAME derived peptides of the invention are obtainable by chemical synthesis and subsequent purification (e.g. see Example 1). The PRAME derived peptides of the invention are preferably soluble in physiologically acceptable watery solutions (e.g. PBS) comprising no more than 35, 20, 10, 5 or 0% DMSO. In such a solution the peptides are preferably soluble at a concentration of at least 0.5, 1, 2, 4, or 8 mg peptide per ml. More preferably, a mixture of more than one different PRAME derived peptides of the invention is soluble at a concentration of at least 0.5, 1, 2, 4, or 8 mg peptide per ml in such solutions.

A preferred use of the peptides according to the invention is their use as a medicament, whereby more preferably the peptides are used as a vaccine or an active component thereof. Each peptide may be either used alone or preferably in combinations of at least one or two or three or four or more than four peptides of the invention, in the treatment and/or prevention of cancer, for the manufacture of medicaments, preferably vaccine for the treatment or prevention of human cancer or neoplastic disease. These diseases preferably comprise hematological malignancies and solid tumors, wherein the cancer cells express the PRAME tumor antigen. Such a medicament and/or anti-tumor vaccine according to the invention may be used to treat patients suffering from or at risk of developing the following, non extensive list of PRAME expressing human neoplastic diseases: melanoma, lymphoma, papillomas, breast or cervical carcinomas, acute and chronic leukemias, medulloblastoma, non-small cell lung carcinoma, head and neck cancer, renal carcinoma, pancreatic carcinoma, prostate cancer, small cell lung cancer, multiple myeloma, sarcomas and hematological malignancies like chronic myeloid leukemia and acute myeloid leukemia.

In a further aspect, the current invention further relates to compositions which may be useful for treatment and/or vaccination of human subjects, comprising at least one, at least two, at least three, at least four peptides according to the invention as defined above and optionally one or more pharmaceutically acceptable excipients, in particular adjuvants and immune modulators. Preferably, the composition is a pharmaceutical composition and/or intended for use as a medicament. The pharmaceutical composition is preferably intended for vaccination. The pharmaceutical composition are preferably used for the treatment and/or prevention of cancer, for the manufacture of medicaments, preferably vaccine for the treatment or prevention of human neoplastic disease or cancer. A non-exhaustive list of neoplastic diseases (cancer) have already been given herein. The composition preferably comprises at least 2, 3, 4, 5, 6, 7, 8, 9, 10, 12, 15 and up to 20 different peptides. Alternatively or in combination with former preferred embodiments, the peptides present in the composition comprises a length of no more than 100 amino acids and comprise a contiguous amino acid sequence from the human PRAME protein selected from the group consisting of amino acid sequences SEQ ID No's 1-20 (as listed in Table 6). More preferably, the peptides present in this composition are selected within the following subgroup: SEQ ID No's 6, 5, 7, 8, 9, 10, 11, 12, 14, 15, 16, and 18. All of them comprise a HLA-A2 or other predominant HLA class I epitope. The most preferred peptides present in the composition of the invention are selected within the following subgroup: SEQ ID No's 6, 5, 8, 14, 15, 16 and 18. Alternatively, 2 or more peptides may be selected to match the HLA alleles of the subject or the population of subjects to be treated.

Formulation of medicaments, ways of administration and the use of pharmaceutically acceptable excipients are known and customary in the art and for instance described in Remington; The Science and Practice of Pharmacy, 21$^{st}$ Edition 2005, University of Sciences in Philadelphia. Pharmaceutical compositions and medicaments of the invention are preferably formulated to be suitable for intravenous or subcutaneous, or intramuscular administration, although other administration routes can be envisaged, such as mucosal administration or intradermal and/or intracutaneous administration, e.g. by injection.

It is furthermore encompassed by the present invention that the administration of at least one peptide and/or at least one composition of the invention may be carried out as a single administration. Alternatively, the administration of at least one peptide and/or at least one composition may be repeated if needed and/or distinct peptides and/or compositions of the invention may be sequentially administered.

The pharmaceutically acceptable composition according to the invention may preferably comprise at least one immune response stimulating compound or adjuvant. Advantageously the pharmaceutical composition according to the invention may additionally comprise one or more synthetic adjuvants. These adjuvants may be admixed to the pharmaceutical composition according to the invention or may be administered separately to the mammal or human to be treated. Particularly preferred are those adjuvants that are known to act via the Toll-like receptors Immune modifying compounds that are capable of activation of the innate immune system, can be activated particularly well via Toll like receptors (TLR's), including TLR's 1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LPA, LTA, fimbriae, outer membrane proteins, heatshock proteins from bacteria or from the host, and Mycobacterial lipoarabinomannans. TLR3 may be activated by dsRNA, in particular of viral origin, or by the chemical compound poly(I:C). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B Streptococcus heat labile soluble factor (GBS-F) or Staphylococcus modulins. TLR7 may be activated by imidazoquinolines. TLR9 may be activated by unmethylated CpG DNA or chromatin—IgG complexes. In particular TLR3, TLR7 and TLR9 play an important role in mediating an innate immune response against viral infections, and compounds capable of activating these receptors are particularly preferred for use in the methods of treatment and in the compositions or medicaments according to the invention. Particularly preferred adjuvants comprise, but are not limited to, synthetically produced compounds comprising dsRNA, poly(I:C), unmethylated CpG DNA which trigger TLR3 and TLR9 receptors, IC31, IMSAVAC, Montanide ISA-51 (an adjuvant produced by Seppic 7, France). In another preferred embodiment, the synthetic adjuvant compounds are physically linked to the peptides of the invention. Physical linkage of adjuvants and costimulatory compounds or functional groups, to the HLA class I and HLA class II epitope comprising peptides provides an enhanced immune response by simultaneous stimulation of antigen presenting cells, in particular dendritic cells, that internalize, metabolize and display antigen.

Furthermore, the use of antigen presenting cell (co)stimulatory molecules, as set out in WO99/61065 and in WO03/084999, in combination with the peptides and compositions of the invention is preferred. In particular the use of 4-1-BB and/or CD40 ligands, agonistic antibodies or functional fragments and derivates thereof, as well as synthetic compounds with similar agonistic activity are preferably administered separately or combined with the peptides of the invention to subjects to be treated in order to further stimulate the mounting of an optimal immune response in the subject.

In addition a preferred embodiment comprises delivery of the peptides, with or without additional immune stimulants such as TLR ligands and/or anti CD40/anti-4-1 BB antibodies in a slow release vehicle such as mineral oil (e.g. Montanide ISA 51) or PGLA.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the elements is present, unless the context clearly requires that there be one and only one of the elements. The indefinite article "a" or "an" thus usually means "at least one".

The invention is further illustrated by the following examples which should not be construed for limiting the scope of the invention.

DESCRIPTION OF THE FIGURES

FIG. 1: Proteasomal cleavage sites within synthetic peptides from the human PRAME protein as determined by in vitro digestions with purified proteasomes (SEQ ID NOS 47-77, respectively, in order of appearance). Major and low abundant cleavage sites (represented by more or less than 5% of the digested material respectively) are indicated by bold and thin arrows respectively.

FIG. 4: Example of intactness of predicted epitopes in fragments of a long PRAME peptide digested by proteasome. Sequences disclosed as SEQ ID NOS 78-79, 51, 80-81, 79 and 82-87, respectively, in order of appearance.

Figure 2:
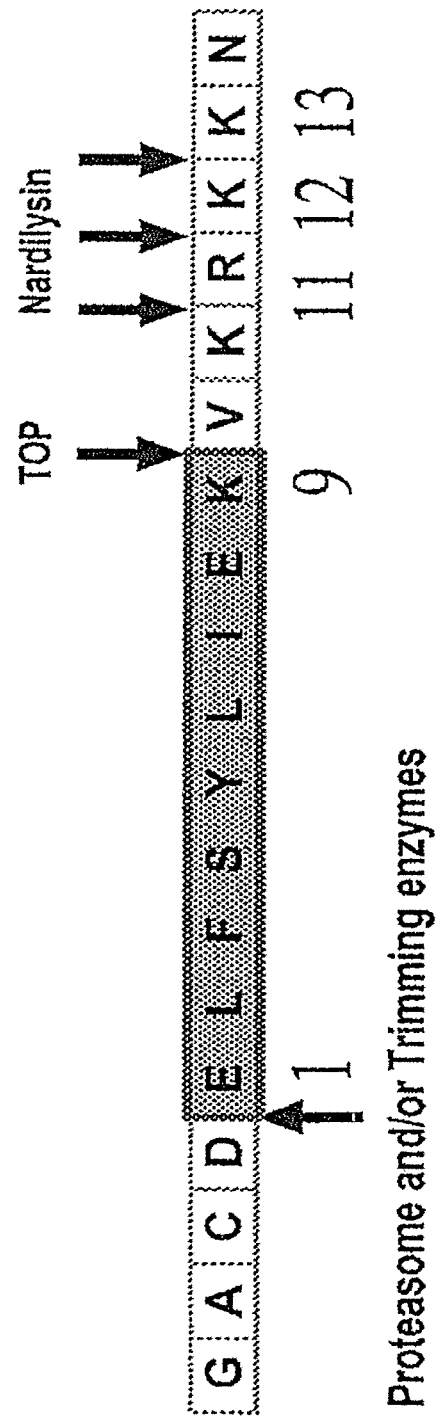
FIG. 2: Enzymatic N-terminal and C-terminal liberation of PRA190-198 as determined by in vitro enzymatic digestion analysis with cytosolic extracts and purified enzymes.

[a] HLA class I binding peptides as determined in competition binding assay (see Tables 3).

[b] Fragments obtained after digestion with immuno-proteasome are ordered according to their C-terminus. Start and end aa. are listed.

[c] Intensity is expressed as % of total summed mass-peak intensities of digested 27-mer at 1 h incubation time.

EXAMPLES

In the current invention the different aspects that are required for the induction of an efficient and successful vaccine-induced T cell response against PRAME expressing cancer cells in patients are combined for the design and selection of optimal PRAME derived vaccine peptides. An optimal PRAME vaccine peptide should encompass at least one, but preferably more, HLA class I presented cytotoxic T lymphocyte (CTL) epitope(s) capable to induce a CTL response in patients, together with at least one PRAME-derived peptide with proven capacity to elicit a CD4[+] Th lymphocyte response. The experimental section provides the parameters required for the optimal design and choice of PRAME derived peptides for vaccination in terms of sequence and length/size. The experimental section discloses both identification and confirmation of HLA class I presented CTL epitopes and CD4[+] Th lymphocyte reactivity inducing peptides, in vitro and in vivo, that are present in the full length PRAME protein and which can be combined in peptides having an optimal length of 19-45 amino acids.

Example 1

Identification of HLA Class I Presented Peptides from PRAME Synthetic Production of Peptides All peptides used in these studies were synthesized by solid phase strategies on an automated multiple peptide synthesizer (Abimed AMS 422) using standard Fmoc chemistry. Short peptides for CTL inductions were dissolved in 20 μA DMSO, diluted in 0.9% NaCl to a peptide concentration of 1 mg/ml and stored at −20° C. before usage. The fluorescein-labeled reference peptides, used in the HLA class I peptide binding assays, were synthesized as Cys-derivative. Labeling was performed with 5-(iodoacetamido) fluorescein (Fluka Chemie AG, Buchs, Switzerland) at pH 7.5 (Na-phosphate in water/acetonitrile 1:1 v/v). The labelled peptides were desalted over Sephadex G-10 and further purified by C18 RP-HPLC. Labelled peptides were analysed by mass spectrometry. The 27-mer and 22-mer polypeptides used for in vitro proteasome digestion analysis and analysis of CD4[+] Th lymphocyte reactivity were synthesized as described above, purified by reversed phase-HPLC in an acetonitrile-water gradient and lyophilized from acetonitrile-water overnight. Purity was confirmed by mass spectrometry.

Pré-Selection of PRAME Peptides for HLA Class I Binding Measurements

A selection of PRAIVIE peptides with a length of 8, 9, 10 or 11 amino acids with potential binding capacity for the HLA class I molecules that are most predominant was made using the peptide binding prediction algorithms BIMAS (Parker, et al., 1994, J. Immunol. 152:163) and SYFPEITHI. These computer algorithms search for peptides contained in the full length PRAME protein complying to the binding motifs of the HLA class I molecule of interest. HLA class I molecules were chosen with high or at least moderate prevalences in the human population, being HLA-A1, HLA-A2, HLA-A3, HLA-A24, HLA-A68, HLA-B7, HLA-B8, HLA-B35, HLA-B60, HLA-B61 and HLA-B62. Prevalences among the human populations of these HLA class I molecules are shown in Table 1 below.

Using the algorithm, the full length PRAME protein was screened for peptides with a predicted (efficient) binding capacity for the chosen HLA class I molecules. The PRAME peptides (length 9, 10 or 11 aa.) with a high predicted binding capacity were synthetically produced to enable actual experimental determination of their binding capacity in competition-based HLA class I binding assays. Because a high prediction score for binding to a certain HLA class I molecule does not necessarily correlate with actual high affinity binding (as has been shown by Kessler et al., 2003, Hum Immunol. 64:245) such binding measurements are required for the assessment of the binding capacity.

TABLE 1

Frequency distribution of HLA I antigens expressed as percentages among major populations[a]

| HLA class I | Population | | | |
|---|---|---|---|---|
| | Black | Caucasoid | Oriental | Amerindian |
| A1 | 9 | 26 | 7 | 11 |
| A2 | 29 | 44 | 47 | 43 |
| A3 | 13 | 22 | 6 | 8 |
| A11 | 3 | 13 | 30 | 4 |
| A24 | 6 | 20 | 42 | 52 |
| A68 | 18 | 8 | 3 | 12 |
| B7 | 15 | 17 | 7 | 5 |
| B8 | 9 | 14 | 3 | 2 |
| B14 | 7 | 6 | 1 | 3 |
| B35 | 11 | 20 | 10 | 32 |
| B60 | 1 | 6 | 17 | 5 |
| B61 | 0 | 6 | 9 | 23 |
| B62 | 2 | 8 | 16 | 21 |

[a]Phenotype frequencies for the HLA antigens have been deduced using the gene frequencies as given by: Marsh et al., The HLA FactsBook., 1999.

Determination of HLA Class I Peptide Binding Capacity

For the experimental measurement of HLA class I binding capacity, HLA class I competition-based cellular binding assays were used that have been developed for HLA-A1, HLA-A2, HLA-A3, HLA-A24, HLA-A68, HLA-B7, HLA-B8, HLA-B35, HLA-B60, HLA-B61 and HLA-B62 (Kessler et al., 2003, Hum Immunol. 64:245). EBV transformed human B cells (B-LCL) were used that were 'stripped' from their naturally presented HLA class I peptides by mild acid treatment. B-LCL were harvested and washed in phosphate buffered saline (PBS) and the pellet (2-15×10[6] cells) was put on ice for 5 min. The elution was performed by incubating the cells for exactly 90 s in ice-cold citric-acid buffer (1:1 mixture of 0.263 M citric acid and 0.123 M $Na_2HPO_4$, adjusted to the pH listed in Table 2) Immediately thereafter, cells were buffered with ice-cold IMDM containing 2% FCS, washed once more in the same medium and resuspended at a concentration of 4×10[5] cells/ml in IMDM medium containing 2% FCS and 2 μg/ml human $\beta_2$-microglublin (($\beta_2$M) (Sigma, St. Louis, Mo., USA).

Eight serial twofold dilutions of each competitor test peptide in PBS/BSA 0.5% were made (highest concentration 600 μM, 6-fold assay concentration). In the assay, test peptides were tested from 100 μM to 0.8 μM. Fluoresceine (F1)-labeled reference peptides that are used in the different HLA class I competition assays and their source are listed in Table 2. These peptides, which have established high binding affinity in the HLA class I molecule under study, were dissolved in PBS/BSA 0.5% at 6-fold final assay concentration. In a well of a 96-well V-bottom plate 25 μl of competitor (test) peptide was mixed with 25 μl F1-labeled reference peptide. Subsequently, the stripped B-LCL were added at 4×10[4]/well in 100 μl/well. After incubation for 24 h at 4° C., cells were washed three times in PBS containing 1% BSA, fixed with 0.5% paraformaldehyde, and analyzed with FACScan flowcytometry (Becton Dickinson) to measure the mean fluorescence (MF). The percentage inhibition of Fl-labeled reference peptide binding was calculated using the following formula:

(1-($MF_{reference+competitor\ peptide}$-$MF_{background}$)/ ($MF_{reference\ peptide}$-$MF_{background}$))×100%.

The binding affinity of competitor peptide is expressed as the concentration that inhibits 50% binding of the Fl-labeled reference peptide ($IC_{50}$). $IC_{50}$ was calculated applying non-lineair regression analysis. An $IC_{50} \leq 5$ μM was considered high affinity binding, 5 μM<$IC_{50}$≤about 15 μM was considered intermediate affinity binding, about 15 μM<$IC_{50}$≤100 μM was judged low affinity binding and $IC_{50}$>100 μM was regarded as no binding.

TABLE 2

Characteristics of the different HLA class I binding assays.

| HLA class I Allele | Reference peptides used in the assays | | | B-LCL cell line used in the assay | |
|---|---|---|---|---|---|
| | FL-labeled seq. (SEQ ID NOS 23-34, respectively, in order of appearance) | [pep.] | Original seq. (SEQ ID NOS 34-46, respectively, in order of appearance) | Name | HLA class I type |
| A1 (A*0101) | YLEPAC(Fl)AKY | 150 nM | YLEPAIAKY | CAA | A*0101, B*0801, Cw*0701 |
| A2 (A*0201) | FLPSDC(Fl)FPSV | 150 nM | FLPSDFFPSV | JY | A*0201, B*0702, Cw*0702 |
| A3 (A*0301) | KVFPC(Fl)ALINK | 150 nM | KVFPYALINK | EKR | A*0301, B*0702, Cw*0702 |
| A11 (A*1101) | KVFPC(Fl)ALINK | 150 nM | KVFPYALINK | BVR | A*1101, B*3501, Cw*0401 |
| A24 (A*2402) | RYLKC(Fl)QQLL | 150 nM | RYLKDQQLL | Vijf | A*2402; B*0702, Cw*0702 |
| A68 (A*6801) | KTGGPIC(Fl)KR | 150 nM | KTGGPIYKR | A68HI | A*6801, B*4402, Cw*0704 |
| B7 (B*0702) | APAPAPC(Fl)WPL | 150 nM | APAPAPSWPL | JY | A*0201, B*0702, Cw*0702 |
| B8 (B*0801) | FLRGRAC(Fl)GL | 50 nM | FLRGRAYGL | Vavy | A*0101, B*0801, Cw*0701 |
| B35 (B*3501) | NPDIVC(Fl)YQY | 150 nM | NPDIVIYQY | BVR | A*1101, B*3501, Cw*0401 |
| B60 (B*4001) | KESTC(Fl)HLVL | 125 nM | KESTLHLVL | DKB | A*2402, B*4001, Cw*0304 |
| B61 (B*4002) | GEFGGC(Fl)GSV | 50 nM | GEFGGFGSV | Swei007 | A*2902, B*4002, Cw*0202 |
| B62 (B*1501) | YLGEFSC(Fl)TY | 150 nM | YLGEFSITY | BSM | A*0201, B*1501, Cw*0304 |

TABLE 3A

High and intermediate binding HLA-A2 (*0201) peptides from PRAME.

| Start[a] | Sequence[b] | Length[c] | Binding ($IC_{50}^{d}$) |
|---|---|---|---|
| 25 | RLVELAGQSL | 10 | 11.1 |
| 33 | SLLKDEALAI | 10 | 14.0 |
| 34 | LLKDEALAI | 9 | 10.2 |
| 39 | ALAIAALEL | 9 | 5.1 |
| 39 | ALAIAALELL | 10 | 9.0 |
| 47 | LLPRELFPPL | 10 | 2.1 |

Results of the HLA Class I Binding Assays

The actual binding measurements revealed that 49 PRAME peptides (9 or 10 aa. long) displayed an high or intermediate affinity for HLA-A2 (Table 3a) and, as shown in Table 3b, 93 peptides (8-, 9-, 10-, 11-mers) had a high or intermediate binding capacity for the other HLA class I molecules (HLA-A1, HLA-A3, HLA-A24, HLA-A68, HLA-B7, HLA-B8, HLA-B35, HLA-B60, HLA-B61 and HLA-B62). These peptides with a proven HLA class I binding capacity were further analysed for their enzymatic liberation from their flanking protein sequence by proteasomal cleavage using the results of the proteasome digestion analysis (FIG. 1). As listed in Table 4, this analysis enabled a selection of the peptides that have (1) a high affinity HLA class I binding capacity, (2) are C-terminal generated by a proteasomal cleavage and (3) are found intact in the proteaome digestion analysis.

TABLE 3A-continued

High and intermediate binding HLA-A2 (*0201) peptides from PRAME.

| Start[a] | Sequence[b] | Length[c] | Binding ($IC_{50}^{d}$) |
|---|---|---|---|
| 71 | AMVQAWPFTC | 10 | 10.4 |
| 91 | HLHLETFKA | 9 | 11.1 |
| 99 | AVLDGLDVL | 9 | 13.4 |
| 99 | AVLDGLDVLL | 10 | 9.4 |
| 100 | VLDGLDVLL | 9 | 5.2 |

TABLE 3A-continued

High and intermediate binding HLA-A2 (*0201) peptides from PRAME.

| Start[a] | Sequence[b] | Length[c] | Binding (IC$_{50}$[d]) |
|---|---|---|---|
| 100 | VLDGLDVLLA | 10 | 11.9 |
| 103 | GLDVLLAQEV | 10 | 15.2 |
| 142 | SLYSFPEPEA | 10 | 1.9 |
| 182 | FLKEGACDEL | 10 | 3.0 |
| 186 | GACDELFSYL | 10 | 10.6 |
| 190 | ELFSYLIEKV | 10 | 4.5 |
| 214 | KIFAMPMQDI | 10 | 7.2 |
| 242 | CTWKLPTLA | 9 | 9.3 |
| 248 | TLAKFSPYL | 9 | 4.6 |
| 258 | QMINLRRLLL | 10 | 4.0 |
| 284 | YIAQFTSQFL | 10 | 10.4 |
| 292 | FLSLQCLQAL | 10 | 2.5 |
| 294 | SLQCLQALYV | 10 | 3.2 |
| 300 | ALYVDSLFF | 9 | 2.7 |
| 300 | ALYVDSLFFL | 10 | 1.7 |
| 301 | LYVDSLFFL | 9 | 6.3 |
| 308 | FLRGRLDQLL | 10 | 9.6 |
| 320 | VMNPLETLSI | 10 | 8.6 |
| 326 | TLSITNCRL | 9 | 13.2 |
| 333 | RLSEGDVMHL | 10 | 6.1 |
| 350 | QLSVLSLSGV | 10 | 13.3 |
| 355 | SLSGVMLTDV | 10 | 9.9 |
| 360 | MLTDVSPEPL | 10 | 5.6 |
| 371 | ALLERASATL | 10 | 12.9 |
| 390 | ITDDQLLAL | 9 | 9.2 |
| 394 | QLLALLPSL | 9 | 2.9 |
| 410 | TLSFYGNSI | 9 | 11.0 |
| 419 | SISALQSLL | 9 | 5.7 |
| 422 | ALQSLLQHL | 9 | 14.2 |
| 422 | ALQSLLQHLI | 10 | 3.2 |
| 425 | SLLQHLIGL | 9 | 3.7 |
| 432 | GLSNLTHVL | 9 | 6.8 |
| 435 | NLTHVLYPV | 9 | 2.5 |
| 454 | TLHLERLAYL | 10 | 12.2 |
| 462 | YLHARLRELL | 10 | 13.3 |
| 462 | YLHARLREL | 9 | 6.2 |
| 466 | RLRELLCEL | 9 | 14.0 |
| 470 | LLCELGRPSM | 10 | 10.5 |

[a]Position in PRAME of the N-terminal amino acid (aa.) of the peptide. Peptides are sorted by their starting aa.
[b]Aa. sequence of the peptide
[c]Length of the peptide
[d]IC$_{50}$ is peptide concentration needed to inhibit binding of FL-labeled reference peptide for 50% (IC$_{50}$ in µM). Peptides with IC$_{50}$ ≤ about 15 µM are considered to be potential CTL epitopes with respect to their binding affinity.

TABLE 3B

High and intermediate affinity binding HLA class I (non HLA-A2) peptides from PRAME.

| Start[a] | Sequence[b] | Length[c] | HLA Class I[d] | Binding (IC$_{50}$[e]) |
|---|---|---|---|---|
| 136 | WSGNRASLY | 9 | HLA-A1 | 4.3 |
| 165 | STEAEQPFI | 9 | HLA-A1 | 1.4 |
| 247 | PTLAKFSPY | 9 | HLA-A1 | 8.5 |
| 267 | LSHIHASSY | 9 | HLA-A1 | 1.0 |
| 275 | YISPEKEEQY | 10 | HLA-A1 | 3.0 |
| 292 | FLSLQCLQALY | 11 | HLA-A1 | 1.0 |
| 293 | LSLQCLQALY | 10 | HLA-A1 | 2.9 |
| 294 | SLQCLQALY | 9 | HLA-A1 | 2.0 |
| 302 | YVDSLFFLR | 9 | HLA-A1 | 1.4 |
| 334 | LSEGDVMHL | 9 | HLA-A1 | 6.3 |
| 361 | LTDVSPEPLQ | 10 | HLA-A1 | 3.8 |
| 361 | LTDVSPEPLQA | 11 | HLA-A1 | 3.5 |
| 390 | ITDDQLLAL | 9 | HLA-A1 | 1.0 |
| 390 | ITDDQLLALL | 10 | HLA-A1 | 1.5 |
| 405 | CSQLTTLSFY | 10 | HLA-A1 | <1 |
| 433 | LSNITHVLY | 9 | HLA-A1 | <1 |
| 439 | VLYPVPLESY | 10 | HLA-A1 | 10.9 |
| 453 | GTLHLERLAY | 10 | HLA-A1 | 2.0 |
| 454 | TLHLERLAY | 9 | HLA-A1 | 10.1 |
| 5 | RLWGSIQSRY | 10 | HLA-A3 | 1.59 |
| 5 | RLWGSIQSR | 9 | HLA-A3 | 1.13 |
| 16 | SMSVWTSPR | 9 | HLA-A3 | <1 |
| 28 | ELAGQSLLK | 9 | HLA-A3 | 3.14 |
| 41 | AIAALELLPR | 10 | HLA-A3 | 10.75 |
| 80 | CLPGVLMK | 9 | HLA-A3 | <1 |
| 107 | LLAQEVRPRR | 10 | HLA-A3 | 14.0 |

TABLE 3B-continued

High and intermediate affinity binding HLA class I (non HLA-A2) peptides from PRAME.

| Start[a] | Sequence[b] | Length[c] | HLA Class I[d] | Binding (IC$_{50}$[e]) |
|---|---|---|---|---|
| 118 | KLQVLDLRK | 9 | HLA-A3 | 2.15 |
| 190 | ELFSYLIEK | 9 | HLA-A3 | 1.42 |
| 194 | YLIEKVKRK | 9 | HLA-A3 | 3.49 |
| 194 | YLIEKVKRKK | 10 | HLA-A3 | 14.00 |
| 198 | KVKRKKNVLR | 10 | HLA-A3 | 7.50 |
| 204 | NVLRLCCKK | 9 | HLA-A3 | 13.50 |
| 205 | VLRLCCKKLK | 10 | HLA-A3 | 1.30 |
| 242 | CTWKLPTLAK | 10 | HLA-A3 | <1 |
| 255 | YLGQMINLRR | 10 | HLA-A3 | 4.50 |
| 261 | NLRRLLLSH | 9 | HLA-A3 | 3.50 |
| 300 | ALYVDSLFF | 9 | HLA-A3 | 8 |
| 333 | RLSEGDVMH | 9 | HLA-A3 | 16.00 |
| 429 | HLIGLSNLTH | 10 | HLA-A3 | 4.00 |
| 432 | GLSNLTHVLY | 10 | HLA-A3 | 4.07 |
| 439 | VLYPVPLESY | 10 | HLA-A3 | 2.67 |
| 459 | RLAYLHARLR | 10 | HLA-A3 | 1.00 |
| 13 | RYISMSVWTS | 10 | HLA-A24 | 5.8 |
| 52 | LFPPLFMAAF | 10 | HLA-A24 | <1 |
| 60 | AFDGRHSQTL | 10 | HLA-A24 | 5.5 |
| 77 | PFTCLPLGVL | 10 | HLA-A24 | 2.1 |
| 85 | VLMKGQHLHL | 10 | HLA-A24 | 15 |
| 96 | TFKAVLDGL | 9 | HLA-A24 | 8.6 |
| 173 | IPVEVLVDLF | 10 | HLA-A24 | <1 |
| 215 | IFAMPMQDI | 9 | HLA-A24 | 1.8 |
| 251 | KFSPYLGQMI | 10 | HLA-A24 | 2.5 |
| 254 | PYLGQMINL | 9 | HLA-A24 | <1 |
| 283 | QYIAQFTSQF | 10 | HLA-A24 | 8.2 |
| 287 | QFTSQFLSL | 9 | HLA-A24 | 1.0 |
| 301 | LYVDSLFFL | 9 | HLA-A24 | <1 |
| 307 | FFLRGRLDQL | 10 | HLA-A24 | 1.8 |
| 412 | SFYGNSISI | 9 | HLA-A24 | <1 |
| 447 | SYEDIHGTL | 9 | HLA-A24 | <1 |
| 459 | RLAYLHARL | 9 | HLA-A24 | <1 |
| 461 | AYLHARLREL | 10 | HLA-A24 | <1 |
| 466 | RLRELLCEL | 9 | HLA-A24 | <1 |
| 494 | TFYDPEPIL | 9 | HLA-A24 | <1 |
| 150 | EAAQPMTKK | 9 | HLA-A*6801 | pred. |
| 150 | EAAQPMTKKR | 10 | HLA-A*6801 | pred. |
| 302 | YVDSLFFLR | 9 | HLA-A*6801 | <1 |
| 113 | RPRRWKLQVL | 10 | HLA-B7 | <1 |
| 113 | RPRRWKLQVL | 10 | HLA-B8 | <1 |
| 258 | QMINLRRLLL | 10 | HLA-B8 | 1.67 |
| 259 | MINLRRLL | 8 | HLA-B8 | <1 |
| 260 | INLRRLLL | 8 | HLA-B8 | <1 |
| 462 | YLHARLREL | 9 | HLA-B8 | <1 |
| 48 | LPRELFPPL | 9 | HLA-B*3501 | <1 |
| 48 | LPRELFPPLF | 10 | HLA-B*3501 | 1.58 |
| 53 | FPPLFMAAF | 9 | HLA-B*3501 | <1 |
| 170 | QPFIPVEVL | 9 | HLA-B*3501 | 2.83 |
| 173 | IPVEVLVDL | 9 | HLA-B*3501 | 2.24 |
| 173 | IPVEVLVDLF | 10 | HLA-B*3501 | <1 |
| 186 | GACDELFSY | 9 | HLA-B*3501 | 2.60 |
| 246 | LPTLAKFSPY | 10 | HLA-B*3501 | <1 |
| 253 | SPYLGQMINL | 10 | HLA-B*3501 | 1.98 |
| 487 | CPHCGDRTFY | 10 | HLA-B*3501 | 1.5 |
| 499 | EPILCPCFM | 9 | HLA-B*3501 | <1 |
| 36 | KDEALAIAAL | 10 | HLA-B60 | 2.91 |
| 37 | DEALAIAAL | 9 | HLA-B60 | 1.55 |
| 50 | RELFPPLFM | 9 | HLA-B60 | 1.48 |
| 448 | YEDIHGTLHL | 10 | HLA-B60 | <1 |
| 37 | DEALAIAAL | 9 | HLA-B61 | <1 |
| 50 | RELFPPLFM | 9 | HLA-B61 | <1 |
| 50 | RELFPPLFMA | 10 | HLA-B61 | <1 |
| 94 | LETFKAVL | 8 | HLA-B61 | <1 |
| 89 | GQHLHLETF | 9 | HLA-B62 | 2.39 |
| 300 | ALYVDSLFF | 9 | HLA-B62 | <1 |
| 316 | LLRHVMNPL | 9 | HLA-B62 | 2.56 |
| 427 | LQHLIGLSNL | 10 | HLA-B62 | 2.41 |
| 439 | VLYPVPLESY | 10 | HLA-B62 | 1.66 |

[a] Postion in PRAME of the N-term; peptides are sorted by HLA molecule and start position.
[b] Amino acid (aa.) sequence of the peptide
[c] Length of the peptide
[d] HLA class I molecule in which the peptide binds
[e] IC$_{50}$: peptide concentration that inhibits binding of FL-labeled reference peptide for 50% (IC$_{50}$ in µM). Peptides with IC50 < about 15 µM are potential CTL epitopes, with respect to their binding affinity. Pred., indicates high binding affinity predicted, but not tested.

Example 2

Determination of Proteasomal Cleavage Sites in Full Length PRAME Materials and Methods In Vitro Proteasome Mediated Cleavage Analysis 20S proteasomes were purified from a B-LCL cell line as described by Groettrup et al. (J. Biol. Chem. 270:23808-23815.; 1995). This cell type is known to contain immunoproteasomes. High LMP2 and 7 content was confirmed by 2-D immuno-blotting. To assess kinetics, digestions were performed with different incubation periods. Peptides (27 mers, 20 µg) were incubated with 1 µg of purified proteasome at 37° C. for 1 h, 4 h and 24 h in 300 µl proteasome digestion buffer as described (Eggers, et al. 1995. J. Exp. Med. 182:1865). Trifluoroacetic acid was added to stop the digestion and samples were stored at −20° C. before mass spectrometric analysis.

Electrospray ionization mass spectrometry was performed on a hybrid quadrupole time-of-flight mass spectromter, a Q-TOF (Micromass), equipped with an on-line nanoelectrospray interface with an approximate flow rate of 250 mL/min. Injections were done with a dedicated micro/nano HPLC autosampler, the FAMOS (LC Packings). Digestion solutions were diluted five times in water-methanol-acetic acid (95:5:1, v/v/v), and trapped on the precolumn (MCA-300-05-C8; LC Packings) in water-methanol-acetic acid (95:5:1, v/v/v). Washing of the precolumn was done for 3 min to remove the buffers present in the digests. Subsequently, the trapped analytes were eluted with a steep gradient going from 70% B to 90% B in 10 min, with a flow of 250 nl/min (A: water-methanol-acetic acid (95:5:1, v/v/v); B: water-methanol-acetic acid (10:90:1, v/v/v)). This low elution rate allows for a few additional MS/MS experiments if necessary during the same elution. Mass spectra were recorded from mass 50-2000 Da every second. The resolution allows direct determination of the monoisotopic mass, also from multiple charged ions. The peaks in the mass spectrum were searched in the digested precursor peptide using the Biolynx/proteins software (Micromass). The intensity of the peaks in the mass spectra was used to establish the relative amounts of peptides generated by proteasome digestion.

Results of In Vitro Proteasome Mediated Cleavage Analysis

Twentynine overlapping PRAME peptides (mostly 27-mers) that cover almost the entire PRAME aa. sequence, were digested in vitro with purified 20S proteasomes. Digestion intervals were 1 hr, 4 hr and 24 hr. Mass spectrometrical analysis of the digestion fragments revealed abundant and low abundant proteasomal cleavage sites within the digested PRAME peptides.

FIG. 1 shows major (represented by more than 5% of the digested material) and low abundant cleavage sites (represented by less than 5% of the digested material) that were found after incubation of the indicated synthetic peptides with purified proteasome for 1 hour. This timepoint reflects most reliably physiological enzymatic activity.

The identification of the peptide fragments generated by in vitro proteasomal cleavage was used to assess the C-terminal generation of the high and intermediate affinity binding HLA class I peptides (Table 3a, 3b) on the one hand and the presence of the epitope as an intact fragment after proteasomal cleavage on the other hand. FIG. 4 shows an example of a binding peptide that is found intact after proteasomal cleavage, representing an epitope that is very likely to occur in vivo and example of a binding peptide that is not retained intact after proteasomal cleavage and therefore less likely to be found in vivo. The PRAME peptides that display high or intermediate affinity HLA class I binding capacity and were found as intact fragment with the correct C-terminal after in vitro proteasomal cleavage are listed in Table 4. This selection of peptides is very likely intracellularly produced and naturally presented in HLA class I molecules on the cell surface of tumor cells, and thus they are preferred to induce CTL responses in patients.

TABLE 4

HLA class I binding peptides from PRAME that are present as intact fragment with the correct C-terminus after proteasomal cleavage.

| Start[a] | End | aa. sequence[b] | HLA Class I[c] | C-term. generation[d] | Intact in fragment[e] |
|---|---|---|---|---|---|
| 16 | 24 | SMSVWTSPR | HLA-A3 | see Ex. 3 (Note[f]) | NT |
| 33 | 42 | SLLKDEALAI | HLA-A2 | ++ | + |
| 34 | 42 | LLKDEALAI | HLA-A2 | ++ | + |
| 36 | 45 | KDEALAIAAL | HLA-B60 | ++ | ND |
| 37 | 45 | DEALAIAAL | HLA-B60 | ++ | ND |
| 37 | 45 | DEALAIAAL | HLA-B61 | ++ | ND |
| 48 | 57 | LPREIFPPLF | HLA-B*3501 | + | ND |
| 50 | 58 | RELFPPLFM | HLA-B60 | ++ | + |
| 50 | 58 | RELFPPLFM | HLA-B61 | ++ | + |
| 50 | 59 | RELFPPLFMA | HLA-B61 | ++ | + |
| 52 | 61 | LFPPLFMAAF | HLA-A24 | ++ | ND |
| 53 | 61 | FPPLFMAAF | HLA-B*3501 | ++ | ND |
| 60 | 69 | AFDGRHSQTL | HLA-A24 | + | + |

TABLE 4-continued

HLA class I binding peptides from PRAME that are present as intact fragment with the correct C-terminus after proteasomal cleavage.

| Start[a] | End | aa. sequence[b] | HLA Class I[c] | C-term. generation[d] | Intact in fragment[e] |
|---|---|---|---|---|---|
| 77 | 86 | PFTCLPLGVL | HLA-A24 | ++ | + |
| 89 | 97 | GQHLHLETF | HLA-B62 | ++ | + |
| 94 | 101 | LETFKAVL | HLA-B61 | ++ | + |
| 99 | 108 | AVLDGLDVLL | HLA-A2 | ++ | + |
| 100 | 108 | VLDGLDVLL | HLA-A2 | ++ | + |
| 113 | 122 | RPRRWKLQVL | HLA-B7 | + | + |
| 113 | 122 | RPRRWKLQVL | HLA-B8 | + | + |
| 142 | 151 | SLYSFPEPEA | HLA-A2 | ++ | + |
| 150 | 158 | EAAQPMTKK | HLA-A*6801 | see Ex. 3 (Note[f]) | NT |
| 150 | 159 | EAAQPMTKKR | HLA-A*6801 | see Ex. 3 (Note[f]) | NT |
| 170 | 178 | QPFIPVEVL | HLA-B*3501 | ++ | ND |
| 190 | 198 | ELFSYLIEK | HLA-A3 | see Ex. 3 (Note[f]) | + |
| 248 | 256 | TLAKFSPYL | HLA-A2 | + | + |
| 254 | 262 | PYLGQMINL | HLA-A24 | +/see Ex. 3 (Note[f]) | + |
| 253 | 262 | SPYLGQMINL | HLA-B*3501 | +/see Ex. 3 (Note[f]) | + |
| 259 | 266 | MINLRRLL | HLA-B8 | + | + |
| 258 | 267 | QMINLRRLLL | HLA-A2 | + | + |
| 258 | 267 | QMINLRRLLL | HLA-B8 | + | + |
| 260 | 267 | INLRRLLL | HLA-B8 | + | + |
| 283 | 292 | QYIAQFTSQF | HLA-A24 | ++ | + |
| 284 | 293 | YIAQFTSQFL | HLA-A2 | ++ | + |
| 287 | 295 | QFTSQFLSL | HLA-A24 | ++ | ND |
| 300 | 308 | ALYVDSLFF | HLA-A2 | + | + |
| 300 | 308 | ALYVDSLFF | HLA-A3 | + | + |
| 300 | 308 | ALYVDSLFF | HLA-B62 | + | + |
| 300 | 309 | ALYVDSLFFL | HLA-A2 | ++ | + |
| 301 | 309 | LYVDSLFFL | HLA-A2 | ++ | + |
| 301 | 309 | LYVDSLFFL | HLA-A24 | ++ | + |
| 326 | 334 | TLSITNCRL | HLA-A2 | ++ | + |
| 334 | 342 | LSEGDVMHL | HLA-A1 | + | + |
| 333 | 342 | RLSEGDVMHL | HLA-A2 | + | + |
| 361 | 370 | LTDVSPEPLQ | HLA-A1 | + | + |
| 361 | 371 | LTDVSPEPLQA | HLA-A1 | + | + |
| 371 | 380 | ALLERASATL | HLA-A2 | ++ | + |
| 390 | 399 | ITDDQLLALL | HLA-A1 | + | + |
| 410 | 418 | TLSFYGNSI | HLA-A2 | ++ | + |

TABLE 4-continued

HLA class I binding peptides from PRAME that are present as intact fragment with the correct C-terminus after proteasomal cleavage.

| Start[a] | End | aa. sequence[b] | HLA Class I[c] | C-term. generation[d] | Intact in fragment[e] |
|---|---|---|---|---|---|
| 412 | 420 | SFYGNSISI | HLA-A24 | ++ | + |
| 425 | 433 | SLLQHLIGL | HLA-A2 | ++ | + |
| 427 | 436 | LQHLIGLSNL | HLA-B62 | + | + |
| 429 | 438 | HLIGLSNLTH | HLA-A3 | + | + |
| 439 | 448 | VLYPVPLESY | HLA-A1 | + | + |
| 439 | 448 | VLYPVPLESY | HLA-A3 | + | + |
| 439 | 448 | VLYPVPLESY | HLA-B62 | + | + |
| 459 | 467 | RLAYLHARL | HLA-A24 | ++ | + |
| 462 | 470 | YLHARLREL | HLA-A2 | + | + |
| 461 | 470 | AYLHARLREL | HLA-A24 | + | + |
| 462 | 470 | YLHARLREL | HLA-B8 | + | + |
| 462 | 471 | YLHARLRELL | HLA-A2 | + | + |

[a]Position in PRAME of the N-terminus of the presented epitope. Peptides are sorted by start aa.
[b]aa. sequence of the peptide.
[c]HLA class I molecule in which the peptide binds.
[d]Generation of C-terminus of the epitope after 1 h digestion: classification: abundant (++) present for >5%, low abundant (+) present for <5%.
[e]Intact epitope found in digestion fragments after 1 h digestion: (+), present; (−), not present; (ND), could not be determined due to artificial ends of the synthetic input peptides; (NT), Not tested, but predicted to be abundantly made by Nardilysin.
[f]The C-terminus of PRA(190-198) is generated by a non-proteasomal cleavage pathway, involving first Nardilysin and subsequently Thimet oligopeptidase (TOP) as explained in Example 3 and FIG. 2. The C-termini of PRA(16-24), PRA(150-158), PRA(150-159), PRA(253-262) and PRA(254-262) are predicted to be made directly by an abundant cleavage site of Nardilysin. The latter two peptides (PRA(253-262), and PRA(254-262)) were, in addition, experimentally shown to be generated by a proteasomal cleavage at their C-terminus.

Example 3

Non-Proteasomal Cleavages are Required to Generate the C-Terminus of Proteasome-Independent HLA-A3-Presented CTL Epitope PRAME 190-198

Some occasional CTL epitopes, mostly with a basic residue at their C-terminus, require non-proteasomal cleavages, by additional enzymes, to liberate their C-terminus (Tenzer et al., 2005; Cell. Mol. Life Sci 62:1025 and Seifert et al., 2003, Nat. Immunol. 4:375). The current invention includes one such a CTL epitope, position 190-198 in PRAME with aa. sequence ELFSYLIEK, of which the C-terminus is generated independently of the proteasome by two consecutive cleavages of Nardilysin (EC 3.4.24.61) and Thimet oligopeptidase (TOP; EC 3.4.24.15).

In addition to its involvement in the production of the ELFSYLIEK epitope, Nardilysin was predicted to efficiently produce by a direct cleavage the C-termini of the HLA-A3 binding peptide PRA$^{16-24}$ (SMSVWTSPR), the HLA-A68 binding peptides PRA$^{150-158}$ and PRA$^{150-159}$ (EAAQPMTKK and EAAQPMTKKR), the HLA-A24 binding peptide PRA$^{254-262}$ and the HLA-B*3501 binding peptide PRA$^{253}$-262. The latter two peptides (PRA$^{254}$-262 and PRA$^{253}$-262) were C-terminally also made by a proteasomal cleavage (as indicated in table 4).

Material and Methods and Results of Determination of Enzymatic Generation of the N-Terminus and C-Terminus of PRAME$^{190-198}$ Purified preparations of Proteasome, Nardilysin and Thimet oligopeptidase (TOP), at a concentration of 20 nM, were used to digest in a cell free system synthetic 27-mer (PRA$^{190-208}$), 19-mer (PRA$^{190-208}$), 13-mer (PRA$^{190-202}$), 12-mer (PRA$^{190-201}$) and 11-mer (PRA$^{190-200}$) peptides (at a concentration of 20 uM) encompassing the HLA-A3 presented CTL epitope ELFSYLIEK (PRA$^{190-198}$) with its natural flanking regions. As summarized in FIG. 2, this comprehensive digestion analysis revealed that the N-terminus of PRA$^{190-198}$ is efficiently liberated by a proteasomal cleavage site. However, in contrast to the vast majority of CTL epitopes, the liberation of the C-terminus required a first cleavage by Nardilysin, generating both the 11-mer, 12-mer and 13-mer precursor-epitope peptides PRA$^{190-200;\ 190-201;\ 190-202}$ followed by a further TOP-mediated degradation of the 11-, 12- and 13-mer precursor peptides to the minimal 9-mer ELFSYLIEK epitope.

In addition, functional recognition experiments using the CTL clone recognizing the ELFSYLIEK epitope (see FIG. 3) of targets cells (PRAME and HLA-A3 positive) with suppressed levels of either Nardilysin or TOP (by RNA-interference methodology) confirmed that these two enzymes were crucially required for the generation of the 9-mer ELFSYLIEK PRA$^{190-198}$ CTL epitope in living cells (data not shown).

Because of the closeness of the binding motif of HLA-A3 to that of HLA-A11, this novel epitope is also claimed as a novel epitope presented by HLA-A11. Target cells expressing HLA-A11 and PRAME were specifically recognized by the CTL anti-ELFSYLIEK (data not shown).

Example 4

Determination of Immunogenicity and Endogenous Production of the Identified CTL Epitopes Lymphocytes The analysis of the immunogenicity was performed for a subset of the identified putative HLA class I presented CTL epitopes Immunogenicity was determined by in vitro inductions of CTL against the synthetically produced CTL epitopes. Moreover, the CTL (clones) that were generated have been tested for their capacity to recognize tumor cells co-expressing PRAME and the correct HLA class I molecule.

CTL bulk cultures were induced against the following selected HLA class I binding PRAME derived CTL epitopes. The peptides $PRA^{100-108}$ (VLDGLDVLL), $PRA^{142-151}$ (SLYSFPEPEA), $PRA^{300-309}$ (ALYVDSLFFL), $PRA^{371-380}$ (ALLERASATL), and $PRA^{425-433}$ (SLLQHLIGL) were chosen because these peptides are predicted CTL epitopes presented in HLA-A2. Furthermore, CTL were induced against $PRA^{190-198}$ (ELFSYLIEK), which is a CTL epitope presented in HLA-A3, $PRA^{113-122}$ (RPRRWKLQVL), which is an HLA-B7 presented epitope, and $PRA^{258-267}$ (QMINLRRLLL), which is predicted to be an HLA-B8 expressed CTL epitope.

Procedure of In Vitro Generation of CTL Clones and Functional CTL Assays

Peripheral blood mononuclear cells (PBMC) for CTL inductions were obtained by the Ficoll-Paque method from blood from healthy donors. To optimally use all APC present in PBMC we developed a culture system that yields a mix of activated B cells and mature DC to be used as APC during the primary induction step. PBMC were separated in a T cell fraction and a fraction containing B cells and monocytes by SRBC-rosetting. The T cell fraction was cryopreserved. The mixture of monocytes and B cells was cultured in 24 wells plates at a concentration of $1 \times 10^6$ cells/well in complete culture medium containing 800 U/ml GM-CSF, 500 U/ml IL-4 (PeproTech Inc.) and 500 ng/ml CD40 mAb (clone B-B20; Serotec) for 6 days. This culture system achieved a threefold effect: i) GM-CSF and IL-4 induced differentiation of monocytes into immature dendritic cells, ii) IL-4 and CD40 mAb caused activation and proliferation of B cells (Schultze, et al. 1997, J. Clin. Invest. 100:2757) and iii) CD40 mAb mediated maturation of immature dendritic cells (Cella, et al. 1996. J Exp Med 184:747). At day 3, cytokines and CD40 mAb were replenished. To further promote CTL inducing capacity, the APC-mix was cultured for an additional 2 days with 0.4 ng/ml LPS (Difco Labs), 500 U/ml IFN (Boehringer Mannheim) and 500 ng/ml CD40 mAb. At day 8 the APC-mix was pulsed with 50 µg/ml peptide (each peptide separately) for 4 h at RT, irradiated (30 Gy) and washed to remove free peptide. The cryopreserved autologous T cell fraction was thawed and depleted from $CD4^+$ T cells using magnetic beads (Dynal). The primary induction was performed in 96 well U-bottom plates. APC at a concentration of 10,000/well were co-cultured with 50,000 $CD8^+$ T cells/well in culture medium, containing 10% human pooled serum (HPS), 5 ng/ml IL-7 (PeproTech) and 0.1 ng/ml IL-12 (Sigma). At day 7 after initiation of induction the CTL micro-cultures were harvested (pooled), washed and restimulated at a concentration of 40,000 responder cells/well of 96-well U-bottom plates in culture medium containing 10% HPS, 5 ng/ml IL-7 and 0.1 ng/ml IL-12. Autologous activated B cells, generated via the protocol described by Schultze et al. (1997, J. Clin. Invest. 100:2757), irradiated (75 Gy) and peptide pulsed (50 µg/ml) for 4 h at RT in culture medium containing 2% FCS and 3 µg/ml β-microglublin (Sigma) after mild acid elution to remove naturally presented peptides from the MHC I molecules (see material and methods MHC binding assay), were used at a concentration of 10,000 cells/well as restimulator APC. Restimulations were repeated at day 14 and 21 in a similar way, with the exception of IL-7 being replaced by 20 IU/ml IL-2 (Chiron Corp.). At day 29, the CTL bulk culture was cloned by standard limiting dilution procedures. CTL clones were maintained by aspecific stimulation every 7 to 12 days using a feeder mixture consisting of allogeneic PBMC and B-LCL in culture medium containing 10% FCS, 1.5% leucoagglutinin (Sigma) and 240 IU/ml IL-2.

For functional analysis of CTL capacity to kill peptide loaded target cells or tumor target cells a standard chromium release assays was used. After $^{51}Cr$ labeling (1 h), target cells (2000/well) were added to various numbers of effector cells in a final volume of 100 µA complete culture medium in 96-well-U-bottom plates. After 4 h incubation at 37° C. supernatants were harvested. The mean % specific lysis of triplicate wells was calculated according to: (Experimental release−Spontaneous release)/(Maximal release−Spontaneous release)×100%.

Results of the Analysis of Immunogenicity and Functional Recognition of Tumor Cells by CTL.

The 8 peptides that were chosen for in vitro CTL inductions, which are $PRA^{100-108}$ (HLA-A2), $PRA^{142-151}$ (HLA-A2), $PRA^{300-309}$ (HLA-A2), $PRA^{371-380}$ (HLA-A2), $PRA^{425-433}$ (HLA-A2), $PRA^{190-198}$ (HLA-A3), $PRA^{113-122}$ (HLA-B7) and $PRA^{258-267}$ (HLA-B8), were all capable to induce bulk CTL cultures that highly specifically recognized the inducing peptide when loaded in the correct HLA class I molecule expressed on B-LCL target cells (data not shown). Subsequently, these CTL bulk cultures were cloned by limiting dilution, and CTL clones were generated.

Figure 3A:
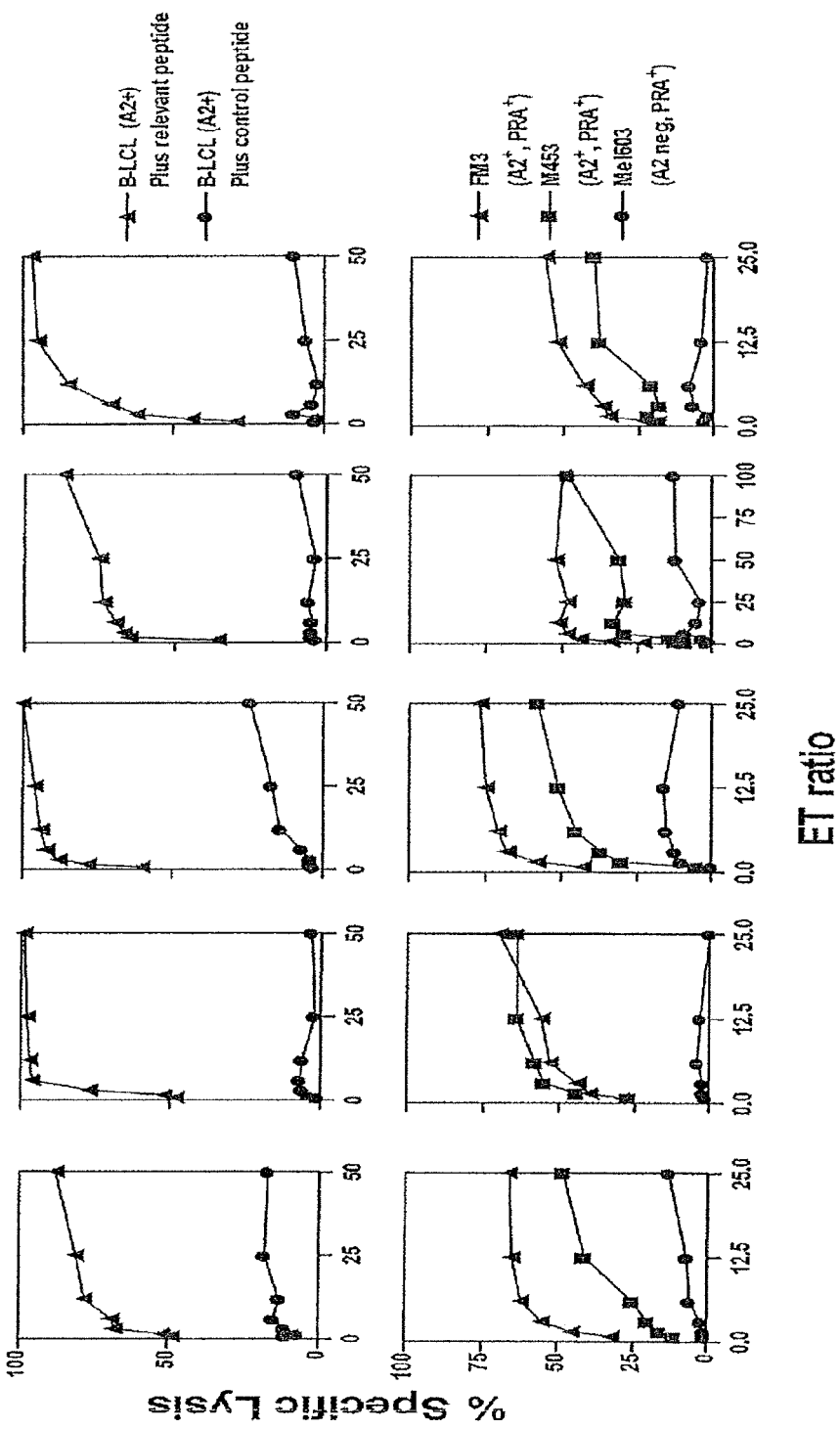
FIG. 3: Specific recognition of peptides and tumor cells by CTL against PRAME derived CTL epitopes as measured in $^{51}$Cr-release cytoxicity assays. Panel A, recognition of HLA-A2 presented epitopes; Panel B, recognition of epitopes presented by other HLA class I molecules.
Figure 3B:
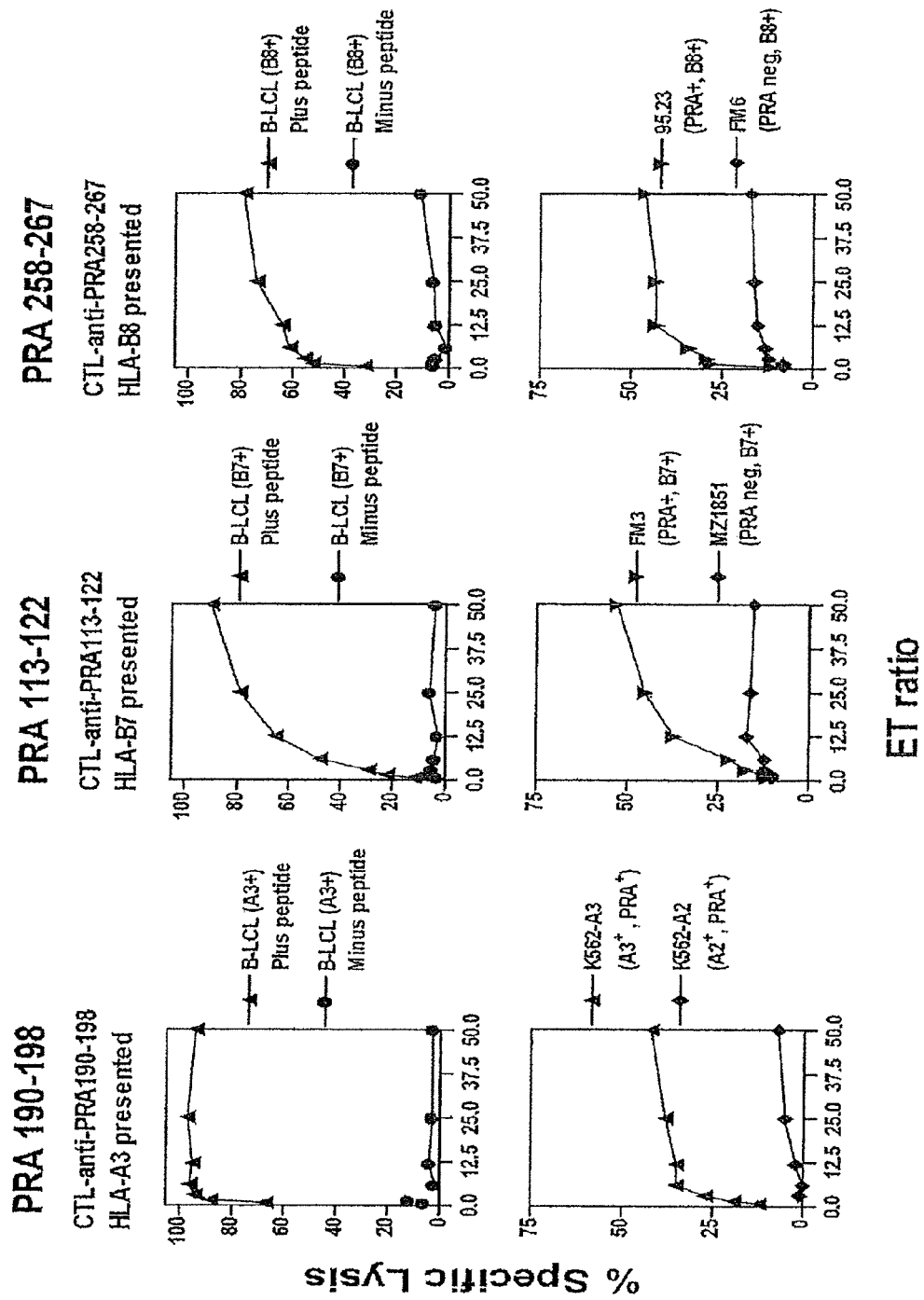

The CTL clones efficiently recognized the CTL epitopes against which they were raised, either as exogenously loaded synthetic peptide (FIGS. 3A and 3B, upper panels) or as endogenously produced and naturally expressed CTL epitope presented on tumor cells (FIGS. 3A and 3B, lower panels). Therefore, both the HLA-A2 presented peptides (FIG. 3A) and the HLA-A3, HLA-B7 and HLA-B8 presented peptides (FIG. 3B) are genuine CTL epitopes. These data confirm the immunogenicity of these 8 CTL epitopes, prove their cell surface expression, and show the accuracy of our CTL epitope predictions. This indicates that all identified predicted CTL epitopes (as listed in Table 4) are very likely tumor cell expressed targets and are suited for the induction of CTL responses in patients with PRAME positive cancers expressing the correct HLA class I molecules.

Example 5

Determination of $CD4^+$ T Helper Cell Reactivity Against HLA Class II Binding Peptides in PRAME For the optimal induction and maintenance of a vaccine induced anti-tumor $CD8^+$ CTL response, capable of eradication of PRAME expressing tumor cells, the induction of a concurrent CD4+ Th response is required (e.g. Bourgeois, et al, 2002. Eur. J. Immunol. 32:2199; Kumaraguru, et al, 2004. J. Immunol. 172:3719; Janssen, et al, 2003. Nature 421:852; Hamilton, et al, 2004. Nat. Immunol. 5:873). The primary mechanism contributing to this phenomenon is the help provided by the CD4+ helper T cell population in the maturation of professional antigen presenting cells—mainly dendritic cells (DCs)—via the CD40-ligand CD40 interaction, which is termed the 'licensing model' (Schoenberger, et al., 1998. Nature 393:480; Lanzavecchia. 1998. Nature 393:413). Several lines of evidence have shown that without such a CD4+ Th response the CD8+ response is not or only suboptimal induced and the maintenance and recall of the memory CD8+ T cell response is compromised (Belz, et al., 2002. J. Virol. 76:12388). It is crucial, therefore, to identify the HLA class II binding peptides in the PRAME protein that are capable of inducing CD4+ Th cells. These PRAME peptides were identified using two different screening assays. Both CD4+ Th cell proliferation and IFNγ produced by Th cells were used to assess the reactivity against a panel of 51 overlapping PRAME peptides with a length needed for HLA class II binding (22-mer or 27-mer peptides). First, the HLA class II molecules that have predicted binding capacity for these overlapping PRAME peptides were identified.

In Silico Determination of HLA Class II Binding Profile of Overlapping Polypeptides (27-mer or 22-mer) Derived from PRAME HLA class II peptide binding is less stringent than HLA class I binding. Peptides binding in HLA class II are at least 13 aa. long and may be much longer because the open end of the HLA class II binding groove allows peptides bound to class II molecules to extend beyond the groove at both ends. Therefore, length requirements of HLA class II binding peptides are much more flexible than the requirements of peptides binding in HLA class I molecules. Furthermore, and in line with this, peptide binding in HLA class II is more promiscuous than binding in HLA class I. Often a polypeptide of a length of 13 to 25 aa. has the capacity to bind in multiple HLA class II molecules. The advantage of these flexible peptide binding characteristics of HLA class II molecules is that actual experimental binding assays are much less needed to verify predicted peptide binding.

For the prediction of HLA class II binding an algorithm that is freely available on the internet was used. This algorithm is 'ProPred' (see Singh et al, 2001, Bioinformatics 17:1236). Using this algorithm, the 51 overlapping peptides were screened for the existence of binding motifs for the different HLA class II molecules and the results were analysed. As shown in Table 5A, all the overlapping peptides that were tested for CD4+ T cell reactivity had a predicted efficient binding capacity for multiple HLA class II molecules (cutoff used: the five predicted best binding peptides from full length PRAME for each class II allele).

TABLE 5A

HLA class II binding capacity of 51 overlapping PRAME peptides

| Pep. No. | Overlapping PRAME peptides (position and length) | | | HLA class II molecules for which the peptide has predicted binding capacity (marked with the symbol X) | | | | | | | | | | | | | |
|---|---|---|---|---|---|---|---|---|---|---|---|---|---|---|---|---|---|
| | Start | End | Length | DR 1 | DR 2 | DR 3 | DR 4 | DR 5 | DR 7 | DR 8 | DR 9 | DR 51 | DR 52 | DR 53 | DQ 2 | DQ 3 | DQ 4 |
| 1 | 1 | 27 | 27 | X | X | X | X | | X | | X | X | | | | | X |
| 2 | 15 | 36 | 22 | X | | X | | X | X | X | | X | X | | | X | X |
| 3 | 19 | 45 | 27 | X | | X | X | X | X | X | | X | X | | X | X | |
| 4 | 31 | 52 | 22 | X | | X | X | | X | X | | X | | | | X | X |
| 5 | 37 | 63 | 27 | X | | X | X | | X | X | | X | | X | X | X | |
| 6 | 48 | 69 | 22 | | | X | X | | | | | | | | X | X | |
| 7 | 53 | 79 | 27 | | X | | X | | | | | X | | | | X | |
| 8 | 66 | 87 | 22 | X | X | | X | | | X | | X | | | | | |
| 9 | 70 | 96 | 27 | X | | | X | | | X | X | X | | | | X | |
| 10 | 84 | 110 | 27 | X | X | | X | | | X | | | X | | | X | X |
| 11 | 95 | 121 | 27 | X | X | X | X | | | X | | X | X | X | X | X | |
| 12 | 98 | 124 | 27 | X | | X | X | | X | X | X | X | | X | X | X | |
| 13 | 110 | 131 | 22 | X | | X | X | X | X | X | X | | | X | | X | X |
| 14 | 116 | 142 | 27 | | | | | X | X | | X | X | | | | X | X |
| 15 | 124 | 145 | 22 | X | X | | X | | | | X | X | | | | X | X |
| 16 | 133 | 159 | 27 | X | X | X | X | | | | | X | | | X | | |
| 17 | 146 | 172 | 27 | | | | X | | | | X | X | | X | | | |
| 18 | 158 | 184 | 27 | | | | X | X | X | | X | X | X | | | | |
| 19 | 173 | 199 | 27 | | | | X | | X | X | | | | | X | X | |
| 20 | 181 | 207 | 27 | X | X | | X | | | X | | X | X | | | X | |
| 21 | 194 | 220 | 27 | X | X | X | X | | | X | | X | X | | | X | |
| 22 | 205 | 231 | 27 | X | | X | X | | X | X | | X | X | X | | X | |
| 23 | 217 | 238 | 22 | | | X | X | | X | X | | X | | | X | X | |
| 24 | 222 | 248 | 27 | | X | X | X | | X | X | | | | X | | X | |
| 25 | 234 | 255 | 22 | | X | X | X | | X | X | | | | | | X | |
| 26 | 239 | 265 | 27 | | X | X | X | | X | | X | X | X | | | X | |
| 27 | 247 | 273 | 27 | X | X | X | X | | X | X | X | X | X | X | | | |
| 28 | 256 | 277 | 22 | X | X | X | X | | X | X | | X | X | X | | | X |
| 29 | 262 | 288 | 27 | X | X | X | X | | X | | | | X | | | X | X |
| 30 | 276 | 302 | 27 | X | X | | X | X | | | X | | | | X | X | X |
| 31 | 290 | 316 | 27 | X | X | X | X | X | X | X | | | X | | X | X | X |
| 32 | 300 | 326 | 27 | | | X | X | | X | X | | | | X | | | X |
| 33 | 311 | 337 | 27 | X | | | X | | X | | X | X | | X | | | |
| 34 | 323 | 349 | 27 | | X | X | | X | | X | | | | | | X | X |
| 35 | 333 | 354 | 22 | X | | X | X | X | X | | | | | | | X | X |
| 36 | 338 | 364 | 27 | | X | X | X | X | X | X | X | | | | | X | X |
| 37 | 353 | 379 | 27 | | X | | X | X | | X | X | | | X | X | X | X |

TABLE 5A-continued

HLA class II binding capacity of 51 overlapping PRAME peptides

| Pep. No. | Overlapping PRAME peptides (position and length) | | | HLA class II molecules for which the peptide has predicted binding capacity (marked with the symbol X) | | | | | | | | | | | | | | |
|---|---|---|---|---|---|---|---|---|---|---|---|---|---|---|---|---|---|---|
| | Start | End | Length | DR 1 | DR 2 | DR 3 | DR 4 | DR 5 | DR 7 | DR 8 | DR 9 | DR 51 | DR 52 | DR 53 | DQ 2 | DQ 3 | DQ 4 |
| 38 | 359 | 385 | 27 | X | | X | X | X | | X | | | | X | X | X | |
| 39 | 372 | 398 | 27 | X | | X | X | | | X | X | | | | | X | |
| 40 | 384 | 410 | 27 | | X | X | X | | | | | | X | | | X | |
| 41 | 395 | 416 | 22 | | | X | X | | | | | | X | | | X | |
| 42 | 399 | 425 | 27 | X | | X | X | | X | X | X | X | | | | X | X |
| 43 | 412 | 433 | 22 | X | | X | X | X | X | X | X | X | | | X | X | X |
| 44 | 415 | 441 | 27 | X | | | X | X | X | X | X | X | | X | X | X | X |
| 45 | 424 | 450 | 27 | | X | X | | | X | X | | | X | X | X | | |
| 46 | 434 | 455 | 22 | | X | X | | | | X | | | | | | | |
| 47 | 442 | 463 | 22 | | X | | | | X | X | | | | X | | | |
| 48 | 447 | 473 | 27 | X | | X | X | | X | X | X | X | X | | X | X | |
| 49 | 460 | 486 | 27 | | X | X | | X | | | X | X | | | X | | |
| 50 | 473 | 499 | 27 | X | | X | X | | | X | | X | | | | | |
| 51 | 483 | 509 | 27 | | | X | | | | X | | | | | | | |

Procedure for CD4+ T Cell Proliferation Assay and CD4+ T Cell IFNγ ELISPOT Assay For the CD4+ T cell proliferation assay, total PBMC (1.5×10e5 cells/well), either obtained from healthy donors or patients with a PRAME-positive cancer, were seeded in 8 wells of a U-bottom 96-wells plate in RPMI culture medium supplemented with 10% autologous serum and 10 ng/ml of 51 overlapping 27-mer or 22-mer PRAME peptides. At day 6, 50 nl of 3H-thymidine (1 mCi/50 ml) was added and at day 7 the incorporation of 3H-thymidine was measured.

For the IFNγ ELISPOT assay, CD45RO+ cells were isolated from PBMC using CD45RO magnetic beads from Miltenyi Biotec. Subsequently, CD45RO+ (and CD45RO-negative) cells were seeded in 10 wells of a 24-wells plate (2–3×10e6 cells/well) together with autologous irradiated PBMC at a ratio of 4:1 in IMDM with 10% human pooled serum supplemented with 10 peptide mixes of 5 different peptides each from the panel of 51 overlapping 27-mer or 22-mer PRAME peptides. The peptide concentration of each peptide was 5 ng/ml, and IL-2 (150 IU/ml) was added at day 2. At day 10, the peptide-stimulated CD45RO cultures were counted and seeded in IFNγ ELISPOT plates together with autologous irradiated PBMC at a ratio of 1:1 in triplicate in the absence of peptide or in the presence of 5 ng/ml of the separate peptides no 1 to no 51.

Results of CD4+ T Cell Reactivity Against the Panel of 51 PRAME 27-mer/22-mer Peptides The analysis of CD4+ Th cell reactivity against 51 overlapping PRAME peptides in peripheral blood of 8 healthy donors and 7 PRAME positive cancer patients, revealed that 28 out of the 51 peptides induced IFNγ production by CD4+ Th cells and 36 peptides induced CD4+ Th cell proliferation (Table 5B).

TABLE 5B

Reactivity of 51 overlapping HLA class II binding PRAME peptides.

| | | | | IFNγ produced by CD4+ Th cells | | | |
|---|---|---|---|---|---|---|---|
| Pep. No. | Pept. position and length | | | Memory fraction in healthy donors | Memory fraction in patients | Naive fraction (in healthy donors | CD4+ Th cell proliferation |
| | Start | End | Length | | | | |
| 1 | 1 | 27 | 27 | + | + | | + |
| 2 | 15 | 36 | 22 | + | + | | + |
| 3 | 19 | 45 | 27 | + | | | + |
| 4 | 31 | 52 | 22 | | | | + |
| 5 | 37 | 63 | 27 | | | | + |
| 6 | 48 | 69 | 22 | + | | | + |
| 7 | 53 | 79 | 27 | + | | | + |
| 8 | 66 | 87 | 22 | + | | + | + |
| 9 | 70 | 96 | 27 | + | | + | + |
| 10 | 84 | 110 | 27 | + | + | | + |
| 11 | 95 | 121 | 27 | | | | + |
| 12 | 98 | 124 | 27 | + | | | + |
| 13 | 110 | 131 | 22 | + | + | + | + |
| 14 | 116 | 142 | 27 | + | | | + |
| 15 | 124 | 145 | 22 | + | | | |
| 16 | 133 | 159 | 27 | + | | | + |
| 17 | 146 | 172 | 27 | | | | |
| 18 | 158 | 184 | 27 | | | | |
| 19 | 173 | 199 | 27 | | | | + |

TABLE 5B-continued

Reactivity of 51 overlapping HLA class II binding PRAME peptides.

| | | | | IFNγ produced by CD4+ Th cells | | | |
|---|---|---|---|---|---|---|---|
| Pep. | Pept. position and length | | | Memory fraction in healthy | Memory fraction in | Naive fraction (in healthy | CD4+ Th cell |
| No. | Start | End | Length | donors | patients | donors | proliferation |
| 20 | 181 | 207 | 27 | + | + | | + |
| 21 | 194 | 220 | 27 | + | + | | |
| 22 | 205 | 231 | 27 | + | + | + | |
| 23 | 217 | 238 | 22 | | | | + |
| 24 | 222 | 248 | 27 | + | | | + |
| 25 | 234 | 255 | 22 | + | | | + |
| 26 | 239 | 265 | 27 | | | | + |
| 27 | 247 | 273 | 27 | + | | | + |
| 28 | 256 | 277 | 22 | + | + | | + |
| 29 | 262 | 288 | 27 | + | + | | |
| 30 | 276 | 302 | 27 | | | | + |
| 31 | 290 | 316 | 27 | | | | + |
| 32 | 300 | 326 | 27 | | | | + |
| 33 | 311 | 337 | 27 | | | | + |
| 34 | 323 | 349 | 27 | | | | + |
| 35 | 333 | 354 | 22 | | | | + |
| 36 | 338 | 364 | 27 | | | | |
| 37 | 353 | 379 | 27 | | + | | + |
| 38 | 359 | 385 | 27 | | | | |
| 39 | 372 | 398 | 27 | | | | |
| 40 | 384 | 410 | 27 | | | | |
| 41 | 395 | 416 | 22 | | | | + |
| 42 | 399 | 425 | 27 | + | | | + |
| 43 | 412 | 433 | 22 | | | | + |
| 44 | 415 | 441 | 27 | | | | |
| 45 | 424 | 450 | 27 | + | | | + |
| 46 | 434 | 455 | 22 | + | | | |
| 47 | 442 | 463 | 22 | | | | |
| 48 | 447 | 473 | 27 | + | | | + |
| 49 | 460 | 486 | 27 | + | | | + |
| 50 | 473 | 499 | 27 | | | | |
| 51 | 483 | 509 | 27 | | + | | |

Example 6

Selection of Vaccine Peptides Fulfilling the Major Vaccine Requirements

An optimal and defined T cell-inducing composition, comprising one or more PRAME derived peptides, inducing an immune response against PRAME positive tumors must induce both an HLA class I restricted CD8+ CTL response and, simultaneously, an HLA class II restricted CD4+ T helper response. The Th cell response is required to enhance the induction and to maintain the CTL response.

Moreover, due to the extensive polymorphism of the HLA molecules, an optimal vaccine needs to be designed in order to have a broad HLA haplotype coverage allowing a use of this vaccine for a large potential population of subjects. Furthermore, the vaccine should be suitable for a high percentage of individual patients with PRAME positive cancers. Therefore, a vaccine composition according to this invention contains multiple PRAME CTL epitopes that are presented in different HLA class I molecules with a high prevalence in the population. Because of the high degree of promiscuous binding in HLA class II molecules, this requirement is less strictly required for CD4+ T helper cell inducing peptides. The identification of CTL epitopes, as summarized in Table 4, and CD4+ T helper epitopes, as listed above in Table 5A and 5B, enabled the design of vaccine peptides to be contained in a defined vaccine for PRAME positive cancers.

The vaccine composition comprises PRAME derived peptides of 30-35 aa. in length, because several advantages are associated with peptides of this size. As mentioned before, such peptides are in principle easy to synthesize. Furthermore, they have sufficient length to contain both HLA class I presented CTL epitopes and HLA class II presented T helper epitopes. Finally, of great importance is that peptides of this length need to be processed by professional antigen presenting cells, in particular dendritic cells, before the epitopes (both CTL and T helper) can be presented by the antigen presenting cell (Zwaveling, et al, 2002. J. Immunol. 169:350). As a consequence, presentation on non-professional antigen presenting cells and systemic spread through the organism will not take place, and therefore, the induction of tolerance, which has been observed after vaccination with minimal HLA class I presented CTL epitopes (Toes, et al, 1996. J. Immunol. 156:3911; Toes, et al, 1996. Proc. Natl. Acad. Sci. U.S.A 93:7855.), will not occur. Therefore, vaccine peptides of this length are superior over short minimal HLA class I epitopes or full length proteins.

Using the information of the identified CD8+ CTL epitopes and CD4+ T helper reactive PRAME derived peptides, 20 PRAME vaccine peptides were designed that comply with the following three major rules: 1) containing at least one CTL epitope, preferably more than one, and most preferably also CTL epitopes of which the immunogenicity was confirmed by CTL inductions and more preferably presentable by HLA-A2, 2) containing at least one CD4+ T helper cell reactive peptide, preferably reactive both in patients having a PRAME positive malignancy and in healthy donors and 3) a length of 19-45 aa., preferably 30 to 35 amino acids.

The PRAME derived peptides listed in Table 6, are designed according to this invention and fulfil to these requirements. The PRAME derived peptides in Table 6 have a superior capacity to mount an effective, enhanced and prolonged immune response against PRAME expressing malignancies and tumors in human subjects in vivo than PRAME fragments and compositions previously described in the art.

Each of the peptides of the invention as listed in Table 6 has actually been synthesized and purified as described in Example 1 herein above. However, for one peptide (SEQ ID NO. 22: amino acids 222-256 of SEQ ID NO. 21), that was initially designed using the same criteria as for the peptides in Table 6, we found that in practice it could not be synthesized in acceptable purity (less than 2% correct sequence). We further note that each of these peptides of the invention is soluble in physiologically acceptable salt solutions (comprising at most 35% DMSO) at concentrations in the range of 0.5-8 mg/ml.

TABLE 6

Twenty PRAME vaccine peptides (ID No's 1-20; length 33-35 aa.) and their characterization with respect to HLA class I and HLA class II presented epitopes contained in the peptides.

| Vaccine peptide[a] (No. and position in PRAME) | HLA class II epitopes contained in vaccine peptide | | HLA class I epitopes contained in vaccine peptide | | | | | HLA class I binding capacity | | | |
|---|---|---|---|---|---|---|---|---|---|---|---|
| | HLA class II Binding Peptide[b] | CD4+ - Th cell Reactivity[c] | Start[d] | End | Sequence[e] | Length[f] | HLA class I allele | Binding (IC50[g]) | Pro- cessing C-term[h] | Intact Frag- ment[i] | CTL[j] |
| # 1 PRAME 1-33 | 1-27 | IFNγ/Prolif | 5 | 14 | RLWGSIQSRY | 10 | HLA-A3 | 1.59 | − | − | n.t. |
| | | | 5 | 13 | RLWGSIQSR | 9 | HLA-A3 | 1.13 | − | − | n.t. |
| | | | 13 | 22 | RYISMSVWTS | 10 | HLA-A24 | 5.8 | − | − | n.t. |
| | | | 16 | 24 | SMSVWTSPR | 9 | HLA-A3 | <1 | +[(k)] | NT | n.t. |
| # 2 PRAME 19-53 | 19-45 | IFNγ/Prolif | 25 | 34 | RLVELAGQSL | 10 | HLA-A2 | 11.1 | − | − | n.t. |
| | | | 28 | 36 | ELAGQSLLK | 9 | HLA-A3 | 3.14 | − | − | n.t. |
| | | | 33 | 42 | SLLKDEALAI | 10 | HLA-A2 | 14.0 | ++ | + | n.t. |
| | | | 34 | 42 | LLKDEALAI | 9 | HLA-A2 | 10.2 | ++ | + | n.t. |
| | | | 36 | 45 | KDEALAIAAL | 10 | HLA-B60 | 2.91 | ++ | ND | n.t. |
| | | | 37 | 45 | DEALAIAAL | 9 | HLA-B60 | 1.55 | ++ | ND | n.t. |
| | | | 37 | 45 | DEALAIAAL | 9 | HLA-B61 | <1 | ++ | ND | n.t. |
| | | | 39 | 47 | ALAIAALEL | 9 | HLA-A2 | 5.1 | − | − | n.t. |
| | | | 39 | 48 | ALAIAALELL | 10 | HLA-A2 | 9.0 | − | − | n.t. |
| | | | 41 | 50 | AIAALELLPR | 10 | HLA-A3 | 10.75 | − | − | n.t. |
| # 3 PRAME 47-79 | 48-69 | IFNγ/Prolif | 47 | 56 | LLPRELFPPL | 10 | HLA-A2 | 2.1 | − | − | − |
| | 53-79 | IFNγ/Prolif | 48 | 56 | LPRELFPPL | 9 | HLA-B*3501 | <1 | − | − | n.t. |
| | | | 48 | 57 | LPREIFPPLF | 10 | HLA-B*3501 | 1.58 | + | ND | n.t. |
| | | | 50 | 58 | RELFPPLFM | 9 | HLA-B60 | 1.48 | ++ | + | n.t. |
| | | | 50 | 58 | RELFPPLFM | 9 | HLA-B61 | <1 | ++ | + | n.t. |
| | | | 50 | 59 | RELFPPLFMA | 10 | HLA-B61 | <1 | ++ | + | n.t. |
| | | | 52 | 61 | LFPPLFMAAF | 10 | HLA-A24 | <1 | ++ | ND | n.t. |
| | | | 53 | 61 | FPPLFMAAF | 9 | HLA-B*3501 | <1 | − | ND | n.t. |
| | | | 60 | 69 | AFDGRHSQTL | 10 | HLA-A24 | 5.5 | + | + | n.t. |
| # 4 PRAME 69-101 | 70-96 | IFNγ/Prolif | 71 | 80 | AMVQAWPFTC | 10 | HLA-A2 | 10.4 | − | − | n.t. |
| | | | 77 | 86 | PFTCLPLGVL | 10 | HLA-A24 | 2.1 | ++ | + | n.t. |
| | | | 80 | 88 | CLPLGVLMK | 9 | HLA-A3 | <1 | − | − | n.t |
| | | | 85 | 94 | VLMKGQHLHL | 10 | HLA-A24 | 15 | − | − | n.t. |
| | | | 89 | 97 | GQHLHLETF | 9 | HLA-B62 | 2.39 | ++ | + | n.t. |
| | | | 91 | 99 | HLHLETFKA | 9 | HLA-A2 | 11.1 | − | − | n.t |
| | | | 94 | 101 | LETFKAVL | 8 | HLA-B61 | <1 | ++ | + | n.t |
| # 5 PRAME 80-114 | 84-110 | IFNγ/Prolif | 80 | 88 | CLPLGVLMK | 9 | HLA-A3 | <1 | − | − | n.t. |
| | | | 85 | 94 | VLMKGQHLHL | 10 | HLA-A24 | 15 | − | − | n.t. |
| | | | 89 | 97 | GQHLHLETF | 9 | HLA-B62 | 2.39 | ++ | + | n.t. |
| | | | 91 | 99 | HLHLETFKA | 9 | HLA-A2 | 11.1 | − | − | n.t. |
| | | | 94 | 101 | LETFKAVL | 8 | HLA-B61 | <1 | ++ | + | n.t. |
| | | | 96 | 104 | TFKAVLDGL | 9 | HLA-A24 | 8.6 | − | − | n.t. |
| | | | 99 | 108 | AVLDGLDVLL | 10 | HLA-A2 | 9.4 | ++ | + | n.t. |
| | | | 99 | 107 | AVLDGLDVL | 9 | HLA-A2 | 13.4 | − | − | n.t. |
| | | | 100 | 108 | VLDGLDVLL | 9 | HLA-A2 | 5.2 | ++ | + | + |
| | | | 100 | 109 | VLDGLDVLLA | 10 | HLA-A2 | 11.9 | − | − | n.t. |
| | | | 103 | 112 | GLDVLLAQEV | 10 | HLA-A2 | 15.2 | − | − | n.t. |

TABLE 6-continued

Twenty PRAME vaccine peptides (ID No's 1-20; length 33-35 aa.) and their characterization with respect to HLA class I and HLA class II presented epitopes contained in the peptides.

| Vaccine peptide[a] (No. and position in PRAME) | HLA class II epitopes contained in vaccine peptide | | HLA class I epitopes contained in vaccine peptide | | | | | HLA class I binding capacity | | | | |
|---|---|---|---|---|---|---|---|---|---|---|---|---|
| | HLA class II Binding Peptide[b] | CD4+ Th cell Reactivity[c] | HLA class I binding peptide | | | | | | | | | |
| | | | Start[d] | End | Sequence[e] | Length[f] | HLA class I allele | Binding (IC$_{50}$[g]) | Pro- cessing C-term[h] | Intact Frag- ment[i] | CTL[j] |
| # 6 PRAME 94-126 | 98-124 | IFNγ/Prolif | 94 | 101 | LETFKAVL | 8 | HLA-B61 | <1 | + | + | n.t. |
| | | | 96 | 104 | TFKAVLDGL | 9 | HLA-A24 | 8.6 | − | − | n.t. |
| | | | 99 | 107 | AVLDGLDVL | 9 | HLA-A2 | 13.4 | − | − | n.t. |
| | | | 99 | 108 | AVLDGLDVLL | 10 | HLA-A2 | 9.4 | ++ | + | n.t. |
| | | | 100 | 108 | VLDGLDVLL | 9 | HLA-A2 | 5.2 | ++ | + | + |
| | | | 100 | 109 | VLDGLDVLLA | 10 | HLA-A2 | 11.9 | − | − | n.t. |
| | | | 103 | 112 | GLDVLLAQEV | 10 | HLA-A2 | 15.2 | − | − | n.t. |
| | | | 107 | 116 | LLAQEVRPRR | 10 | HLA-A3 | 14.0 | − | − | n.t. |
| | | | 113 | 122 | RPRRWKLQVL | 10 | HLA-B7 | <1 | + | + | + |
| | | | 113 | 122 | RPRRWKLQVL | 10 | HLA-B8 | <1 | + | + | n.t. |
| | | | 118 | 126 | KLQVLDLRK | 9 | HLA-A3 | 2.15 | − | − | n.t. |
| # 7 PRAME 112-144 | 116-142 | IFNγ/Prolif | 113 | 122 | RPRRWKLQVL | 10 | HLA-B7 | <1 | + | + | + |
| | | | 113 | 122 | RPRRWKLQVL | 10 | HLA-B8 | <1 | + | + | n.t. |
| | | | 118 | 126 | KLQVLDLRK | 9 | HLA-A3 | 2.15 | − | − | n.t. |
| | | | 136 | 144 | WSGNRASLY | 9 | HLA-A1 | 4.3 | − | − | n.t. |
| # 8 PRAME 133-166 | 133-159 | IFNγ/Prolif | 136 | 144 | WSGNRASLY | 9 | HLA-A1 | 4.3 | − | − | n.t. |
| | | | 142 | 151 | SLYSFPEPEA | 10 | HLA-A2 | 1.9 | ++ | + | + |
| | | | 150 | 158 | EAAQPMTKK | 9 | HLA-A*6801 | Pred. | +[(k)] | NT | n.t. |
| | | | 150 | 159 | EAAQPMTKKR | 10 | HLA-A*6801 | Pred. | +[(k)] | NT | n.t. |
| # 9 PRAME 173-207 | 181-207 | IFNγ/Prolif | 173 | 182 | IPVEVLVDLF | 10 | HLA-A24 | <1 | − | − | n.t. |
| | | | 182 | 191 | FLKEGACDEL | 10 | HLA-A2 | 3.0 | − | − | n.t. |
| | | | 186 | 195 | GACDELFSYL | 10 | HLA-A2 | 10.6 | − | − | n.t. |
| | | | 186 | 194 | GACDELFSY | 9 | HLA-B*3501 | 2.60 | + | − | n.t. |
| | | | 190 | 199 | ELFSYLIEKV | 10 | HLA-A2 | 4.5 | − | − | n.t. |
| | | | 190 | 198 | ELFSYLIEK | 9 | HLA-A3 | 1.42 | +[(k)] | | + |
| | | | 194 | 202 | YLIEKVKRK | 9 | HLA-A3 | 3.49 | − | − | n.t. |
| | | | 194 | 203 | YLIEKVKRKK | 10 | HLA-A3 | 14.0 | − | − | n.t. |
| | | | 198 | 207 | KVKRKKNVLR | 10 | HLA-A3 | 7.5 | − | − | n.t. |
| # 10 PRAME 190-223 | 194-220 | IFNγ | 190 | 199 | ELFSYLIEKV | 10 | HLA-A2 | 4.5 | − | − | n.t. |
| | | | 190 | 198 | ELFSYLIEK | 9 | HLA-A3 | 1.42 | +[(k)] | + | + |
| | | | 194 | 202 | YLIEKVKRK | 9 | HLA-A3 | 3.49 | − | − | n.t. |
| | | | 194 | 203 | YLIEKVKRKK | 10 | HLA-A3 | 14.0 | − | − | n.t. |
| | | | 198 | 207 | KVKRKKNVLR | 10 | HLA-A3 | 7.5 | − | − | n.t. |
| | | | 204 | 212 | NVLRLCCKK | 9 | HLA-A3 | 13.5 | − | − | n.t. |
| | | | 205 | 214 | VLRLCCKKLK | 10 | HLA-A3 | 1.3 | − | − | n.t. |
| | | | 214 | 223 | KIFAMPMQDI | 10 | HLA-A2 | 7.2 | − | − | n.t. |
| | | | 215 | 223 | IFAMPMQDI | 9 | HLA-A24 | 1.8 | − | − | n.t. |
| # 11 PRAME 234-268 | 234-255 | IFNγ/Prolif | 242 | 250 | CTWKLPTLA | 9 | HLA-A2 | 9.3 | − | − | n.t. |
| | | | 242 | 251 | CTWKLPTLAK | 10 | HLA-A3 | 0.7 | − | − | n.t. |
| | | | 246 | 255 | LPTLAKFSPY | 10 | HLA-B*3501 | 0.11 | − | − | n.t. |
| | | | 247 | 255 | PTLAKFSPY | 9 | HLA-A1 | 8.5 | − | − | n.t. |
| | | | 248 | 256 | TLAKFSPYL | 9 | HLA-A2 | 4.6 | + | + | n.t. |
| | | | 251 | 260 | KFSPYLGQMI | 10 | HLA-A24 | 2.5 | − | − | n.t. |
| | | | 253 | 262 | SPYLGQMINL | 10 | HLA-B*3501 | 1.98 | +[(k)] | + | n.t. |
| | | | 254 | 262 | PYLGQMINL | 9 | HLA-A24 | <1 | +[(k)] | + | n.t. |
| | | | 255 | 264 | YLGQMINLRR | 10 | HLA-A3 | 4.5 | − | − | n.t. |
| | | | 258 | 267 | QMINLRRLLL | 10 | HLA-A2 | 4.0 | + | + | n.t. |
| | | | 258 | 267 | QMINLRRLLL | 10 | HLA-B8 | 1.67 | + | + | + |
| | | | 259 | 266 | MINLRRLL | 8 | HLA-B8 | <1 | + | + | n.t. |
| | | | 260 | 267 | INLRRLLL | 8 | HLA-B8 | <1 | + | + | n.t. |
| # 12 PRAME 247-279 | 247-273 256-277 | IFNγ/Prolif IFNγ/Prolif | 248 | 256 | TLAKFSPYL | 9 | HLA-A2 | 4.6 | + | + | n.t. |
| | | | 251 | 260 | KFSPYLGQMI | 10 | HLA-A24 | 2.5 | − | − | n.t. |
| | | | 253 | 262 | SPYLGQMINL | 10 | HLA-B*3501 | 1.98 | +[(k)] | + | n.t. |
| | | | 254 | 262 | PYLGQMINL | 9 | HLA-A24 | <1 | +[(k)] | + | n.t. |
| | | | 255 | 264 | YLGQMINLRR | 10 | HLA-A3 | 4.5 | − | − | n.t. |
| | | | 258 | 267 | QMINLRRLLL | 10 | HLA-A2 | 4.0 | + | + | n.t. |
| | | | 258 | 267 | QMINLRRLLL | 10 | HLA-B8 | 1.67 | + | + | + |

TABLE 6-continued

Twenty PRAME vaccine peptides (ID No's 1-20; length 33-35 aa.) and their characterization with respect to HLA class I and HLA class II presented epitopes contained in the peptides.

| Vaccine peptide[a] (No. and position in PRAME) | HLA class II epitopes contained in vaccine peptide | | HLA class I epitopes contained in vaccine peptide | | | | HLA class I binding capacity | | | | |
|---|---|---|---|---|---|---|---|---|---|---|---|
| | HLA class II Binding Peptide[b] | CD4+ -Th cell Reactivity[c] | HLA class I binding peptide | | | | HLA class I allele | Binding (IC$_{50}$[g]) | Processing C-term[h] | Intact Fragment[i] | CTL[j] |
| | | | Start[d] | End | Sequence[e] | Length[f] | | | | | |
| | | | 259 | 266 | MINLRRLL | 8 | HLA-B8 | <1 | + | + | n.t. |
| | | | 260 | 267 | INLRRLLL | 8 | HLA-B8 | <1 | + | + | n.t. |
| | | | 261 | 269 | NLRRLLLSH | 9 | HLA-A3 | 3.5 | − | − | n.t. |
| | | | 267 | 275 | LSHIHASSY | 9 | HLA-A1 | 1.0 | − | − | n.t. |
| # 13 PRAME 262-294 | 262-288 | IFNγ | 267 | 275 | LSHIHASSY | 9 | HLA-A1 | 1.0 | − | − | n.t. |
| | | | 275 | 284 | YISPEKEEQY | 10 | HLA-A1 | 3.0 | − | − | n.t. |
| | | | 283 | 292 | QYIAQFTSQF | 10 | HLA-A24 | 8.2 | ++ | + | n.t. |
| | | | 284 | 293 | YIAQFTSQFL | 10 | HLA-A2 | 10.4 | ++ | + | n.t. |
| # 14 PRAME 284-316 | 290-316 | Prolif. | 284 | 293 | YIAQFTSQFL | 10 | HLA-A2 | 10.4 | ++ | + | n.t. |
| | | | 287 | 295 | QFTSQFLSL | 9 | HLA-A24 | 1.0 | ++ | ND | n.t. |
| | | | 292 | 301 | FLSLQCLQAL | 10 | HLA-A2 | 2.5 | − | − | n.t. |
| | | | 292 | 302 | FLSLQCLQALY | 11 | HLA-A1 | 1.0 | − | − | n.t. |
| | | | 293 | 302 | LSLQCLQALY | 10 | HLA-A1 | 2.9 | − | − | n.t. |
| | | | 294 | 302 | SLQCLQALY | 9 | HLA-A1 | 2.0 | − | − | n.t. |
| | | | 294 | 303 | SLQCLQALYV | 10 | HLA-A2 | 3.2 | + | − | n.t. |
| | | | 300 | 308 | ALYVDSLFF | 9 | HLA-A2 | 2.7 | + | + | n.t. |
| | | | 300 | 308 | ALYVDSLFF | 9 | HLA-A3 | 8 | + | + | n.t. |
| | | | 300 | 308 | ALYVDSLFF | 9 | HLA-B62 | <1 | + | + | n.t. |
| | | | 300 | 309 | ALYVDSLFFL | 10 | HLA-A2 | 1.7 | ++ | + | + |
| | | | 301 | 309 | LYVDSLFFL | 9 | HLA-A2 | 6.3 | ++ | + | n.t. |
| | | | 301 | 309 | LYVDSLFFL | 9 | HLA-A24 | <1 | ++ | + | n.t. |
| | | | 302 | 310 | YVDSLFFLR | 9 | HLA-A1 | 1.4 | + | − | n.t. |
| | | | 302 | 310 | YVDSLFFLR | 9 | HLA-A*6801 | <1 | + | − | n.t. |
| | | | 307 | 316 | FFLRGRLDQL | 10 | HLA-A24 | 1.8 | − | − | n.t. |
| # 15 PRAME 295-327 | 300-326 | Prolif. | 300 | 308 | ALYVDSLFF | 9 | HLA-A2 | 2.7 | + | + | n.t. |
| | | | 300 | 308 | ALYVDSLFF | 9 | HLA-A3 | 8 | + | + | n.t. |
| | | | 300 | 308 | ALYVDSLFF | 9 | HLA-B62 | <1 | + | + | n.t. |
| | | | 300 | 309 | ALYVDSLFFL | 10 | HLA-A2 | 1.7 | ++ | + | + |
| | | | 301 | 309 | LYVDSLFFL | 9 | HLA-A2 | 6.3 | ++ | + | n.t. |
| | | | 301 | 309 | LYVDSLFFL | 9 | HLA-A24 | <1 | ++ | + | n.t. |
| | | | 302 | 310 | YVDSLFFLR | 9 | HLA-A1 | 1.4 | + | − | n.t. |
| | | | 302 | 310 | YVDSLFFLR | 9 | HLA-A*6801 | <1 | + | − | n.t. |
| | | | 307 | 316 | FFLRGRLDQL | 10 | HLA-A24 | 1.8 | − | − | n.t. |
| | | | 308 | 317 | FLRGRLDQLL | 10 | HLA-A2 | 9.6 | − | − | n.t. |
| | | | 316 | 324 | LLRHVMNPL | 9 | HLA-B62 | 2.56 | − | − | n.t. |
| # 16 PRAME 353-387 | 353-379 | IFNγ/Prolif | 355 | 364 | SLSGVMLTDV | 10 | HLA-A2 | 9.9 | − | − | n.t. |
| | | | 360 | 369 | MLTDVSPEPL | 10 | HLA-A2 | 5.6 | − | − | n.t. |
| | | | 361 | 370 | LTDVSPEPLQ | 10 | HLA-A1 | 3.8 | + | + | n.t. |
| | | | 361 | 371 | LTDVSPEPLQA | 11 | HLA-A1 | 3.5 | + | + | n.t. |
| | | | 371 | 380 | ALLERASATL | 10 | HLA-A2 | 12.9 | ++ | + | + |
| # 17 PRAME 399-431 | 399-425 | IFNγ/Prolif | 405 | 414 | CSQLTTLSFY | 10 | HLA-A1 | <1 | ++ | − | n.t. |
| | | | 410 | 418 | TLSFYGNSI | 9 | HLA-A2 | 11.0 | − | − | n.t. |
| | | | 412 | 420 | SFYGNSISI | 9 | HLA-A24 | <1 | ++ | + | n.t. |
| | | | 419 | 427 | SISALQSLL | 9 | HLA-A2 | 5.7 | − | − | n.t. |
| | | | 422 | 431 | ALQSLLGHLI | 10 | HLA-A2 | 3.2 | − | − | n.t. |
| | | | 422 | 430 | ALQSLLQHL | 9 | HLA-A2 | 14.2 | − | − | n.t. |
| # 18 PRAME 417-450 | 424-450 | IFNγ/Prolif | 419 | 427 | SISALQSLL | 9 | HLA-A2 | 5.7 | − | − | n.t. |
| | | | 422 | 431 | ALQSLLQHLI | 10 | HLA-A2 | 3.2 | − | − | n.t. |
| | | | 422 | 430 | ALQSLLQHL | 9 | HLA-A2 | 14.2 | − | − | n.t. |
| | | | 425 | 433 | SLLQHLIGL | 9 | HLA-A2 | 3.7 | ++ | + | + |
| | | | 427 | 436 | LQHLIGLSNL | 10 | HLA-B62 | 2.41 | + | + | n.t. |
| | | | 429 | 438 | HLIGLSNLTH | 10 | HLA-A3 | 4.0 | + | + | n.t. |
| | | | 432 | 440 | GLSNLTHVL | 9 | HLA-A3 | 6.8 | + | − | n.t. |
| | | | 432 | 441 | GLSNLTHVLY | 10 | HLA-A3 | 4.07 | − | − | n.t. |
| | | | 433 | 441 | LSNLTHVLY | 9 | HLA-A1 | <1 | − | − | n.t. |
| | | | 435 | 443 | NLTHVLYPV | 9 | HLA-A2 | 2.5 | − | − | n.t. |
| | | | 439 | 448 | VLYPVPLESY | 10 | HLA-A1 | 10.9 | + | + | n.t. |

TABLE 6-continued

Twenty PRAME vaccine peptides (ID No's 1-20; length 33-35 aa.) and their characterization with respect to HLA class I and HLA class II presented epitopes contained in the peptides.

| Vaccine peptide[a] (No. and position in PRAME) | HLA class II epitopes contained in vaccine peptide | | HLA class I epitopes contained in vaccine peptide | | | | | | | | |
|---|---|---|---|---|---|---|---|---|---|---|---|
| | HLA class II Binding Peptide[b] | CD4[+] - Th cell Reactivity[c] | Start[d] | End | Sequence[e] | Length[f] | HLA class I allele | HLA class I binding capacity (IC$_{50}$[g]) | Pro- cessing C-term[h] | Intact Frag- ment[i] | CTL[j] |
| | | | 439 | 448 | VLYPVPLESY | 10 | HLA-A3 | 2.67 | + | + | n.t. |
| | | | 439 | 448 | VLYPVPLESY | 10 | HLA-B62 | 1.66 | + | + | n.t. |
| # 19 PRAME 447-480 | 447-473 | IFNγ/Prolif | 447 | 455 | SYEDIHGTL | 9 | HLA-A24 | <1 | − | − | n.t. |
| | | | 448 | 457 | YEDIHGTLHL | 10 | HLA-B60 | <1 | ++ | − | n.t. |
| | | | 453 | 462 | GTLHLERLAY | 10 | HLA-A1 | 2.0 | − | − | n.t. |
| | | | 454 | 462 | TLHLERLAY | 9 | HLA-A1 | 10.1 | − | − | n.t. |
| | | | 454 | 463 | TLHLERLAYL | 10 | HLA-A2 | 12.2 | − | − | n.t. |
| | | | 459 | 467 | RLAYLHARL | 9 | HLA-A24 | <1 | ++ | + | n.t. |
| | | | 459 | 468 | RLAYLHARLR | 10 | HLA-A3 | 1.0 | − | − | n.t. |
| | | | 461 | 470 | AYLHARLREL | 10 | HLA-A24 | 1 | + | + | n.t. |
| | | | 462 | 470 | YLHARLREL | 9 | HLA-A2 | 6.2 | + | + | n.t. |
| | | | 462 | 470 | YLHARLREL | 9 | HLA-B8 | <1 | + | + | n.t. |
| | | | 462 | 471 | YLHARLRELL | 10 | HLA-A2 | 13.3 | + | + | n.t. |
| | | | 466 | 474 | RLRELLCEL | 9 | HLA-A2 | 14.0 | − | − | n.t. |
| | | | 466 | 474 | RLRELLCEL | 9 | HLA-A24 | <1 | − | − | n.t. |
| | | | 470 | 479 | LLCELGRPSM | 10 | HLA-A2 | 10.5 | − | − | n.t. |
| # 20 PRAME 477-509 | 483-509 | IFNγ | 487 | 496 | CPHCGDRTFY | 10 | HLA-B*3501 | 1.5 | − | − | n.t. |
| | | | 494 | 502 | TFYDPEPIL | 9 | HLA-A24 | <1 | − | − | n.t. |
| | | | 499 | 507 | EPILCPCFM | 9 | HLA-B*3501 | 0.32 | − | − | n.t. |

[a]Vaccine peptides of 33 to 35 aa. length: peptide ID No. and positions of first and last aa. in full length PRAME protein.
[b]Start and end position (aa.) of the HLA class II binding peptide that was tested for CD4[+] Th cell reactivity.
[c]CD4[+] Th cell reactivity against HLA class II binding peptides. Nomenclature: IFNγ: IFNγ-response observed after stimulation with the indicated peptide; Prolif.: Proliferative response observed after stimulation with indicated peptide.
[d]Postion in PRAME of the N-terminal amino acid of the HLA class I binding peptide. Peptides are sorted by the starting aa.
[e]Aa. sequence of the HLA class I binding peptide
[f]Length of the HLA class I binding peptide
[g]IC$_{50}$ is the peptide concentration needed to inhibit binding of FL-labeled reference peptide for 50% (IC$_{50}$ in mM). Pred., predicted high binding affinity.
[h]Generation by proteasome-mediated digestion of fragments containing the correct C-terminus of the HLA class I binding peptide. Digestion was assessed at 1 h digestion because this is physiologically the most relevant time point. Classification: (++) fragments present for >5%, (+) present for <5%, (−) no fragments containing the C-term. were found. Peptides with IC$_{50}$ < 15 mM are considered to be potential CTL epitopes with respect to their binding affinity.
[i]Intact epitope found in digestion fragments after 1 h digestion: (+), present; (−), not present; (ND), could not be determined due to artificial ends of the synthetic input peptides; (NT), intactness of these epitopes after digestion with nardilysin was not tested.
[j]CTL induced against this specific HLA/peptide combination, specifically recognizing tumor cells. Classification: +, CTL induced and recognize tumor cells; −, CTL induced but do not recognize tumor cells; n.t., not tested
[k]HLA-A3 presented CTL epitope PRA(190-198) (ELFSYLIEK) is generated by non-proteasomal cleavages as explained in Example 3 and FIG. 2. The C-termini of PRA(16-24), PRA(150-158), PRA(150-159), PRA(253-262) and PRA(254-262) are predicted to be made directly by an abundant cleavage site of Nardilysin. The latter two peptides (PRA(253-262), and PRA(254-262)) were, in addition, experimentally shown to be generated by a proteasomal cleavage at their C-terminus (see table 4).

The invention claimed is:

1. A method for the treatment of cancer in which the human PRAME protein is overexpressed, comprising administering to a subject in need thereof an immunogenic composition comprising peptides having a length between 33 and 35 contiguous amino acids from the amino acid sequence of human PRAME protein, wherein the peptide comprises at least one HLA class II epitope and at least one HLA class I epitope from the amino acid sequence of the human PRAME protein, and wherein the peptides are selected from the group consisting of SEQ ID Nos: 5, 6, 7, 8, 9, 10, 11, 12, 14, 15, 16, and 18.

2. The method according to claim 1, wherein the cancer is selected from the group consisting of melanoma, lymphoma, papillomas, breast or cervical carcinomas, acute and chronic leukemias, medulloblastoma, non-small cell lung carcinoma, head and neck cancer, renal carcinoma, pancreatic carcinoma, prostate cancer, small cell lung cancer, multiple myeloma, sarcomas and hematological malignancies, chronic myeloid leukemia, and acute myeloid leukemia.

3. The method according to claim 1, wherein the HLA class II epitope is capable of activating a CD4$^+$ Th cell in human cancer patient and/or a healthy control.

4. The method according to claim 1, wherein the HLA class II epitope is capable of activating a CD45RO positive CD4$^+$ Th cell.

5. The method according to claim 1, wherein the HLA class I epitope is C-terminally processed by proteasomal cleavage.

6. The method according to claim 5, wherein the HLA class I epitope is capable of activating a $CD8^+$ CTL in human cancer patient and/or in a healthy control.

7. The method according to claim 1, wherein the contiguous amino acid sequence is selected from the group consisting of amino acid sequences SEQ ID NOs: 5, 6, 8, 14, 15, 16 and 18.

8. The method according to claim 1, wherein the immunogenic composition further comprises at least one additional different peptide selected from the group consisting of SEQ ID Nos: 5, 6, 7, 8, 9, 10, 11, 12, 14, 15, 16, and 18.

9. The method according to claim 1, wherein the composition further comprises at least one adjuvant.

10. The method according to claim 9, wherein the adjuvant acts via a Toll-like receptor.

\* \* \* \* \*

SEQUENCE LISTING

<160> NUMBER OF SEQ ID NOS: 87

<210> SEQ ID NO 1
<211> LENGTH: 33
<212> TYPE: PRT
<213> ORGANISM: Homo sapiens

<400> SEQUENCE: 1

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser

<210> SEQ ID NO 2
<211> LENGTH: 35
<212> TYPE: PRT
<213> ORGANISM: Homo sapiens

<400> SEQUENCE: 2

Val Trp Thr Ser Pro Arg Arg Leu Val Glu Leu Ala Gly Gln Ser Leu
1               5                   10                  15

Leu Lys Asp Glu Ala Leu Ala Ile Ala Ala Leu Glu Leu Leu Pro Arg
            20                  25                  30

Glu Leu Phe
        35

<210> SEQ ID NO 3
<211> LENGTH: 33
<212> TYPE: PRT
<213> ORGANISM: Homo sapiens

<400> SEQUENCE: 3

Leu Leu Pro Arg Glu Leu Phe Pro Pro Leu Phe Met Ala Ala Phe Asp
1               5                   10                  15

Gly Arg His Ser Gln Thr Leu Lys Ala Met Val Gln Ala Trp Pro Phe
            20                  25                  30

Thr

<210> SEQ ID NO 4
<211> LENGTH: 33
<212> TYPE: PRT
<213> ORGANISM: Homo sapiens

<400> SEQUENCE: 4

Leu Lys Ala Met Val Gln Ala Trp Pro Phe Thr Cys Leu Pro Leu Gly
1               5                   10                  15

Val Leu Met Lys Gly Gln His Leu His Leu Glu Thr Phe Lys Ala Val
            20                  25                  30

Leu

<210> SEQ ID NO 5
<211> LENGTH: 35
<212> TYPE: PRT
<213> ORGANISM: Homo sapiens

<400> SEQUENCE: 5

Cys Leu Pro Leu Gly Val Leu Met Lys Gly Gln His Leu His Leu Glu
1               5                   10                  15

Thr Phe Lys Ala Val Leu Asp Gly Leu Asp Val Leu Leu Ala Gln Glu
            20                  25                  30

Val Arg Pro
        35

<210> SEQ ID NO 6
<211> LENGTH: 33
<212> TYPE: PRT
<213> ORGANISM: Homo sapiens

<400> SEQUENCE: 6

Leu Glu Thr Phe Lys Ala Val Leu Asp Gly Leu Asp Val Leu Leu Ala
1               5                   10                  15

Gln Glu Val Arg Pro Arg Arg Trp Lys Leu Gln Val Leu Asp Leu Arg
            20                  25                  30

Lys

<210> SEQ ID NO 7
<211> LENGTH: 33
<212> TYPE: PRT
<213> ORGANISM: Homo sapiens

<400> SEQUENCE: 7

Val Arg Pro Arg Arg Trp Lys Leu Gln Val Leu Asp Leu Arg Lys Asn
1               5                   10                  15

Ser His Gln Asp Phe Trp Thr Val Trp Ser Gly Asn Arg Ala Ser Leu
            20                  25                  30

Tyr

<210> SEQ ID NO 8
<211> LENGTH: 34
<212> TYPE: PRT
<213> ORGANISM: Homo sapiens

<400> SEQUENCE: 8

Trp Thr Val Trp Ser Gly Asn Arg Ala Ser Leu Tyr Ser Phe Pro Glu
1               5                   10                  15

Pro Glu Ala Ala Gln Pro Met Thr Lys Lys Arg Lys Val Asp Gly Leu
            20                  25                  30

Ser Thr

<210> SEQ ID NO 9
<211> LENGTH: 35
<212> TYPE: PRT
<213> ORGANISM: Homo sapiens

<400> SEQUENCE: 9

Ile Pro Val Glu Val Leu Val Asp Leu Phe Leu Lys Glu Gly Ala Cys
1               5                   10                  15

Asp Glu Leu Phe Ser Tyr Leu Ile Glu Lys Val Lys Arg Lys Lys Asn
            20                  25                  30

Val Leu Arg
        35

<210> SEQ ID NO 10
<211> LENGTH: 34
<212> TYPE: PRT
<213> ORGANISM: Homo sapiens

<400> SEQUENCE: 10

Glu Leu Phe Ser Tyr Leu Ile Glu Lys Val Lys Arg Lys Lys Asn Val
1               5                   10                  15

Leu Arg Leu Cys Cys Lys Lys Leu Lys Ile Phe Ala Met Pro Met Gln
            20                  25                  30

Asp Ile

<210> SEQ ID NO 11
<211> LENGTH: 35
<212> TYPE: PRT
<213> ORGANISM: Homo sapiens

<400> SEQUENCE: 11

Ser Ile Glu Asp Leu Glu Val Thr Cys Thr Trp Lys Leu Pro Thr Leu
1               5                   10                  15

Ala Lys Phe Ser Pro Tyr Leu Gly Gln Met Ile Asn Leu Arg Arg Leu
            20                  25                  30

Leu Leu Ser
        35

<210> SEQ ID NO 12
<211> LENGTH: 33
<212> TYPE: PRT
<213> ORGANISM: Homo sapiens

<400> SEQUENCE: 12

Pro Thr Leu Ala Lys Phe Ser Pro Tyr Leu Gly Gln Met Ile Asn Leu
1               5                   10                  15

Arg Arg Leu Leu Leu Ser His Ile His Ala Ser Ser Tyr Ile Ser Pro
            20                  25                  30

Glu

<210> SEQ ID NO 13
<211> LENGTH: 33
<212> TYPE: PRT
<213> ORGANISM: Homo sapiens

<400> SEQUENCE: 13

Leu Arg Arg Leu Leu Leu Ser His Ile His Ala Ser Ser Tyr Ile Ser
1               5                   10                  15

Pro Glu Lys Glu Gln Tyr Ile Ala Gln Phe Thr Ser Gln Phe Leu
            20                  25                  30

Ser

<210> SEQ ID NO 14
<211> LENGTH: 33
<212> TYPE: PRT
<213> ORGANISM: Homo sapiens

<400> SEQUENCE: 14

Tyr Ile Ala Gln Phe Thr Ser Gln Phe Leu Ser Leu Gln Cys Leu Gln
1               5                   10                  15

Ala Leu Tyr Val Asp Ser Leu Phe Phe Leu Arg Gly Arg Leu Asp Gln
            20                  25                  30

Leu

<210> SEQ ID NO 15
<211> LENGTH: 33
<212> TYPE: PRT
<213> ORGANISM: Homo sapiens

<400> SEQUENCE: 15

Leu Gln Cys Leu Gln Ala Leu Tyr Val Asp Ser Leu Phe Phe Leu Arg
1               5                   10                  15

Gly Arg Leu Asp Gln Leu Leu Arg His Val Met Asn Pro Leu Glu Thr
            20                  25                  30

Leu

<210> SEQ ID NO 16
<211> LENGTH: 35
<212> TYPE: PRT
<213> ORGANISM: Homo sapiens

<400> SEQUENCE: 16

Val Leu Ser Leu Ser Gly Val Met Leu Thr Asp Val Ser Pro Glu Pro

-continued

```
                1               5                  10                    15
Leu Gln Ala Leu Leu Glu Arg Ala Ser Ala Thr Leu Gln Asp Leu Val
                  20                25                30

Phe Asp Glu
        35

<210> SEQ ID NO 17
<211> LENGTH: 33
<212> TYPE: PRT
<213> ORGANISM: Homo sapiens

<400> SEQUENCE: 17

Leu Pro Ser Leu Ser His Cys Ser Gln Leu Thr Thr Leu Ser Phe Tyr
1               5                  10                    15

Gly Asn Ser Ile Ser Ile Ser Ala Leu Gln Ser Leu Leu Gln His Leu
                  20                25                30

Ile

<210> SEQ ID NO 18
<211> LENGTH: 34
<212> TYPE: PRT
<213> ORGANISM: Homo sapiens

<400> SEQUENCE: 18

Ser Ile Ser Ile Ser Ala Leu Gln Ser Leu Leu Gln His Leu Ile Gly
1               5                  10                    15

Leu Ser Asn Leu Thr His Val Leu Tyr Pro Val Pro Leu Glu Ser Tyr
                  20                25                30

Glu Asp

<210> SEQ ID NO 19
<211> LENGTH: 34
<212> TYPE: PRT
<213> ORGANISM: Homo sapiens

<400> SEQUENCE: 19

Ser Tyr Glu Asp Ile His Gly Thr Leu His Leu Glu Arg Leu Ala Tyr
1               5                  10                    15

Leu His Ala Arg Leu Arg Glu Leu Leu Cys Glu Leu Gly Arg Pro Ser
                  20                25                30

Met Val

<210> SEQ ID NO 20
<211> LENGTH: 33
<212> TYPE: PRT
<213> ORGANISM: Homo sapiens

<400> SEQUENCE: 20

Pro Ser Met Val Trp Leu Ser Ala Asn Pro Cys Pro His Cys Gly Asp
1               5                  10                    15

Arg Thr Phe Tyr Asp Pro Glu Pro Ile Leu Cys Pro Cys Phe Met Pro
                  20                25                30

Asn

<210> SEQ ID NO 21
<211> LENGTH: 509
<212> TYPE: PRT
<213> ORGANISM: Homo sapiens

<400> SEQUENCE: 21
```

```
Met Glu Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
            20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
50                      55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
                115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
                180                 185                 190

Ser Tyr Leu Ile Glu Lys Val Lys Arg Lys Lys Asn Val Leu Arg Leu
                195                 200                 205

Cys Cys Lys Lys Leu Lys Ile Phe Ala Met Pro Met Gln Asp Ile Lys
        210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
                260                 265                 270

Ser Ser Tyr Ile Ser Pro Glu Lys Glu Glu Gln Tyr Ile Ala Gln Phe
        275                 280                 285

Thr Ser Gln Phe Leu Ser Leu Gln Cys Leu Gln Ala Leu Tyr Val Asp
        290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
                340                 345                 350

Val Leu Ser Leu Ser Gly Val Met Leu Thr Asp Val Ser Pro Glu Pro
            355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
            405                 410                 415
```

```
Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
            435                 440                 445

Glu Asp Ile His Gly Thr Leu His Leu Glu Arg Leu Ala Tyr Leu His
            450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
            485                 490                 495

Asp Pro Glu Pro Ile Leu Cys Pro Cys Phe Met Pro Asn
            500                 505
```

```
<210> SEQ ID NO 22
<211> LENGTH: 35
<212> TYPE: PRT
<213> ORGANISM: Homo sapiens

<400> SEQUENCE: 22

Asp Ile Lys Met Ile Leu Lys Met Val Gln Leu Asp Ser Ile Glu Asp
1               5                   10                  15

Leu Glu Val Thr Cys Thr Trp Lys Leu Pro Thr Leu Ala Lys Phe Ser
            20                  25                  30

Pro Tyr Leu
        35
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Fl labeled Cys

<400> SEQUENCE: 23

Tyr Leu Glu Pro Ala Cys Ala Lys Tyr
1               5
```

```
<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Fl labeled Cys

<400> SEQUENCE: 24

Phe Leu Pro Ser Asp Cys Phe Pro Ser Val
1               5                   10
```

```
<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Fl labeled Cys

<400> SEQUENCE: 25

Lys Val Phe Pro Cys Ala Leu Ile Asn Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fl labeled Cys

<400> SEQUENCE: 26

Lys Val Phe Pro Cys Ala Leu Ile Asn Lys
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fl labeled Cys

<400> SEQUENCE: 27

Arg Tyr Leu Lys Cys Gln Gln Leu Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Fl labeled Cys

<400> SEQUENCE: 28

Lys Thr Gly Gly Pro Ile Cys Lys Arg
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Fl labeled Cys

<400> SEQUENCE: 29
```

```
Ala Pro Ala Pro Ala Pro Cys Trp Pro Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Fl labeled Cys

<400> SEQUENCE: 30

Phe Leu Arg Gly Arg Ala Cys Gly Leu
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Fl labeled Cys

<400> SEQUENCE: 31

Asn Pro Asp Ile Val Cys Tyr Gln Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Fl labeled Cys

<400> SEQUENCE: 32

Lys Glu Ser Thr Cys His Leu Val Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Fl labeled Cys

<400> SEQUENCE: 33

Gly Glu Phe Gly Gly Cys Gly Ser Val
1               5

<210> SEQ ID NO 34
<211> LENGTH: 9
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Fl labeled Cys

<400> SEQUENCE: 34

Tyr Leu Gly Glu Phe Ser Cys Thr Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Leu Glu Pro Ala Ile Ala Lys Tyr
1               5

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Phe Leu Pro Ser Asp Phe Phe Pro Ser Val
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Val Phe Pro Tyr Ala Leu Ile Asn Lys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Val Phe Pro Tyr Ala Leu Ile Asn Lys
1               5                   10

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 39

Arg Tyr Leu Lys Asp Gln Gln Leu Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Thr Gly Gly Pro Ile Tyr Lys Arg
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Pro Ala Pro Ala Pro Ser Trp Pro Leu
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Phe Leu Arg Gly Arg Ala Tyr Gly Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Asn Pro Asp Ile Val Ile Tyr Gln Tyr
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Glu Ser Thr Leu His Leu Val Leu
1               5

<210> SEQ ID NO 45
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 45

Gly Glu Phe Gly Gly Phe Gly Ser Val
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Leu Gly Glu Phe Ser Ile Thr Tyr
1               5

<210> SEQ ID NO 47
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val
            20                  25

<210> SEQ ID NO 48
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Val Trp Thr Ser Pro Arg Arg Leu Val Glu Leu Ala Gly Gln Ser Leu
1               5                   10                  15

Leu Lys Asp Glu Ala Leu Ala Ile Ala Ala Leu
            20                  25

<210> SEQ ID NO 49
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Asp Glu Ala Leu Ala Ile Ala Ala Leu Glu Leu Leu Pro Arg Glu Leu
1               5                   10                  15

Phe Pro Pro Leu Phe Met Ala Ala Phe Asp Gly
            20                  25

<210> SEQ ID NO 50
<211> LENGTH: 27
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 50

Phe Pro Pro Leu Phe Met Ala Ala Phe Asp Gly Arg His Ser Gln Thr
1               5                   10                  15

Leu Lys Ala Met Val Gln Ala Trp Pro Phe Thr
            20                  25

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Ala Met Val Gln Ala Trp Pro Phe Thr Cys Leu Pro Leu Gly Val
1               5                   10                  15

Leu Met Lys Gly Gln His Leu His Leu Glu Thr
            20                  25

<210> SEQ ID NO 52
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Val Leu Met Lys Gly Gln His Leu His Leu Glu Thr Phe Lys Ala
1               5                   10                  15

Val Leu Asp Gly Leu Asp Val Leu Leu Ala Gln
            20                  25

<210> SEQ ID NO 53
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln His Leu His Leu Glu Thr Phe Lys Ala Val Leu Asp Gly Leu Asp
1               5                   10                  15

Val Leu Leu Ala Gln Glu Val Arg Pro Arg Arg
            20                  25

<210> SEQ ID NO 54
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Ala Val Leu Asp Gly Leu Asp Val Leu Leu Ala Gln Glu Val Arg
1               5                   10                  15

Pro Arg Arg Trp Lys Leu Gln Val Leu Asp Leu
```

20                  25

<210> SEQ ID NO 55
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Trp Lys Leu Gln Val Leu Asp Leu Arg Lys Asn Ser His Gln Asp
1               5                   10                  15

Phe Trp Thr Val Trp Ser Gly Asn Arg Ala Ser
                20                  25

<210> SEQ ID NO 56
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Thr Val Trp Ser Gly Asn Arg Ala Ser Leu Tyr Ser Phe Pro Glu
1               5                   10                  15

Pro Glu Ala Ala Gln Pro Met Thr Lys Lys Arg
                20                  25

<210> SEQ ID NO 57
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Pro Met Thr Lys Lys Arg Lys Val Asp Gly Leu Ser Thr Glu Ala
1               5                   10                  15

Glu Gln Pro Phe Ile Pro Val Glu Val Leu Val
                20                  25

<210> SEQ ID NO 58
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Pro Val Glu Val Leu Val Asp Leu Phe Leu Lys Glu Gly Ala Cys
1               5                   10                  15

Asp Glu Leu Phe Ser Tyr Leu Ile Glu Lys Val
                20                  25

<210> SEQ ID NO 59
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 59

Phe Leu Lys Glu Gly Ala Cys Asp Glu Leu Phe Ser Tyr Leu Ile Glu
1               5                   10                  15
Lys Val Lys Arg Lys Lys Asn Val Leu Arg Leu
            20                  25

<210> SEQ ID NO 60
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Asn Val Leu Arg Leu Cys Cys Lys Lys Leu Lys Ile Phe Ala Met
1               5                   10                  15
Pro Met Gln Asp Ile Lys Met Ile Leu Lys Met
            20                  25

<210> SEQ ID NO 61
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Glu Val Thr Cys Thr Trp Lys Leu Pro Thr Leu Ala Lys Phe Ser Pro
1               5                   10                  15
Tyr Leu Gly Gln Met Ile Asn Leu Arg Arg Leu
            20                  25

<210> SEQ ID NO 62
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Thr Leu Ala Lys Phe Ser Pro Tyr Leu Gly Gln Met Ile Asn Leu
1               5                   10                  15
Arg Arg Leu Leu Leu Ser His Ile His Ala Ser
            20                  25

<210> SEQ ID NO 63
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

His Ile His Ala Ser Ser Tyr Ile Ser Pro Glu Lys Glu Glu Gln Tyr
1               5                   10                  15
Ile Ala Gln Phe Thr Ser Gln Phe Leu Ser Leu
            20                  25

<210> SEQ ID NO 64
<211> LENGTH: 27
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Gln Phe Leu Ser Leu Gln Cys Leu Gln Ala Leu Tyr Val Asp Ser
1               5                   10                  15

Leu Phe Phe Leu Arg Gly Arg Leu Asp Gln Leu
            20                  25

<210> SEQ ID NO 65
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Arg Leu Asp Gln Leu Leu Arg His Val Met Asn Pro Leu Glu Thr
1               5                   10                  15

Leu Ser Ile Thr Asn Cys Arg Leu Ser Glu Gly
            20                  25

<210> SEQ ID NO 66
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Leu Glu Thr Leu Ser Ile Thr Asn Cys Arg Leu Ser Glu Gly Asp
1               5                   10                  15

Val Met His Leu Ser Gln Ser Pro Ser Val Ser
            20                  25

<210> SEQ ID NO 67
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Gln Ser Pro Ser Val Ser Gln Leu Ser Val Leu Ser Leu Ser Gly
1               5                   10                  15

Val Met Leu Thr Asp Val Ser
            20

<210> SEQ ID NO 68
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Met Leu Thr Asp Val Ser Pro Glu Pro Leu Gln Ala Leu Leu Glu
1               5                   10                  15
```

Arg Ala Ser Ala Thr Leu Gln Asp Leu Val Phe
            20                  25

<210> SEQ ID NO 69
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Leu Glu Arg Ala Ser Ala Thr Leu Gln Asp Leu Val Phe Asp Glu
1               5                   10                  15

Cys Gly Ile Thr Asp Asp Gln Leu Leu Ala Leu
            20                  25

<210> SEQ ID NO 70
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Phe Asp Glu Cys Gly Ile Thr Asp Asp Gln Leu Leu Ala Leu Leu
1               5                   10                  15

Pro Ser Leu Ser His Cys Ser Gln Leu Thr Thr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Leu Pro Ser Leu Ser His Cys Ser Gln Leu Thr Thr Leu Ser Phe Tyr
1               5                   10                  15

Gly Asn Ser Ile Ser Ile Ser Ala Leu
            20                  25

<210> SEQ ID NO 72
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Asn Ser Ile Ser Ile Ser Ala Leu Gln Ser Leu Leu Gln His Leu
1               5                   10                  15

Ile Gly Leu Ser Asn Leu Thr His Val Leu Tyr
            20                  25

<210> SEQ ID NO 73
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Ser Leu Leu Gln His Leu Ile Gly Leu Ser Asn Leu Thr His Val
1               5                   10                  15

Leu Tyr Pro Val Pro Leu Glu Ser Tyr Glu Asp
            20                  25

<210> SEQ ID NO 74
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Leu Glu Ser Tyr Glu Asp Ile His Gly Thr Leu His Leu Glu Arg
1               5                   10                  15

Leu Ala Tyr Leu His Ala Arg Leu Arg Glu Leu
            20                  25

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Leu Ala Tyr Leu His Ala Arg Leu Arg Glu Leu Leu Cys Glu Leu Gly
1               5                   10                  15

Arg Pro Ser Met Val Trp Leu Ser Ala Asn Pro
            20                  25

<210> SEQ ID NO 76
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Leu Gly Arg Pro Ser Met Val Trp Leu Ser Ala Asn Pro Cys Pro
1               5                   10                  15

His Cys Gly Asp Arg Thr Phe Tyr Asp Pro Glu
            20                  25

<210> SEQ ID NO 77
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Ala Asn Pro Cys Pro His Cys Gly Asp Arg Thr Phe Tyr Asp Pro
1               5                   10                  15

Glu Pro Ile Leu Cys Pro Cys Phe Met Pro Asn
            20                  25

<210> SEQ ID NO 78

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Cys Leu Pro Leu Gly Val Leu Met Lys
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Pro Phe Thr Cys Leu Pro Leu Gly Val Leu
1               5                   10

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Val Gln Ala Trp
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Trp Pro Phe
1

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Thr Cys Leu Pro Leu Gly Val Leu
1               5

<210> SEQ ID NO 83
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

```
Pro Leu Gly Val Leu Met
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Val Leu Met Lys
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Val Leu Met Lys Gly
1               5

<210> SEQ ID NO 86
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Pro Phe Thr Cys Leu Pro Leu Gly Val Leu Met Lys Gly Gln His Leu
1               5                   10                  15

His Leu Glu Thr
            20

<210> SEQ ID NO 87
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Pro Leu Gly Val Leu Met Lys Gly Gln His Leu His Leu Glu Thr
1               5                   10                  15
```